(12) United States Patent
McGrath et al.

(10) Patent No.: US 9,425,413 B2
(45) Date of Patent: Aug. 23, 2016

(54) CONJUGATED SIDE-STRAPPED PHTHALOCYANINES AND METHODS FOR PRODUCING AND USING THE SAME

(71) Applicant: THE ARIZONA BOARD OF REGENTS ON BEHALF OF THE UNIVERSITY OF ARIZONA, Tucson, AZ (US)

(72) Inventors: Dominic V. McGrath, Tucson, AZ (US); Neal R. Armstrong, Tucson, AZ (US)

(73) Assignee: The Arizona Board of Regents on Behalf of the University of Arizona, Tucson, AZ (US)

( * ) Notice: Subject to any disclaimer, the term of this patent is extended or adjusted under 35 U.S.C. 154(b) by 0 days.

(21) Appl. No.: 14/672,124

(22) Filed: Mar. 28, 2015

(65) Prior Publication Data

US 2015/0280143 A1  Oct. 1, 2015

Related U.S. Application Data

(60) Provisional application No. 61/972,230, filed on Mar. 29, 2014.

(51) Int. Cl.
  *H01L 51/00* (2006.01)
  *H01L 51/42* (2006.01)
  *C07D 487/22* (2006.01)

(52) U.S. Cl.
  CPC .......... *H01L 51/0078* (2013.01); *C07D 487/22* (2013.01); *H01L 51/4253* (2013.01); *Y02E 10/549* (2013.01)

(58) Field of Classification Search
  CPC ............ H01L 51/0078; H01L 51/5056; H01L 51/4253; C07F 9/005; C07F 5/003; C07F 7/28; C07F 5/069; C07D 487/22; Y02E 10/549
  See application file for complete search history.

(56) References Cited

PUBLICATIONS

Kobayashi, N., "Adjacent versus opposite type di-aromatic ring-fused phthalocyanine derivatives: synthesis, spectroscopy, electrochemistry, and molecular orbital calculations." Journal of the American Chemical Society 124.27 (2002): 8007-8020.*

* cited by examiner

*Primary Examiner* — Samantha Shterengarts
*Assistant Examiner* — Matt Mauro
(74) *Attorney, Agent, or Firm* — Don D. Cha; Hamilton DeSanctis & Cha, LLP

(57) ABSTRACT

The present invention provides conjugated side-strapped phthalocyanines and methods for producing and using the same. In one particular embodiment, the conjugated side-strapped phthalocyanine is of the formula:

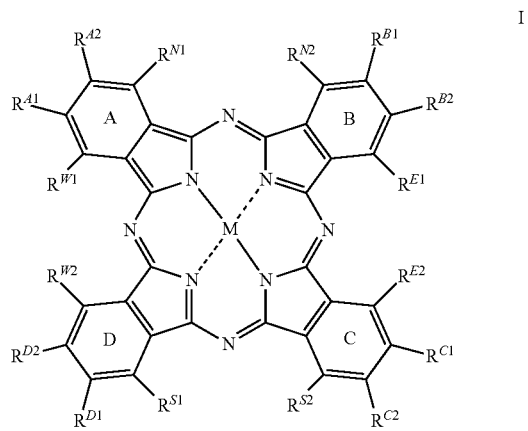

where each of the substituents are defined herein.

13 Claims, 5 Drawing Sheets

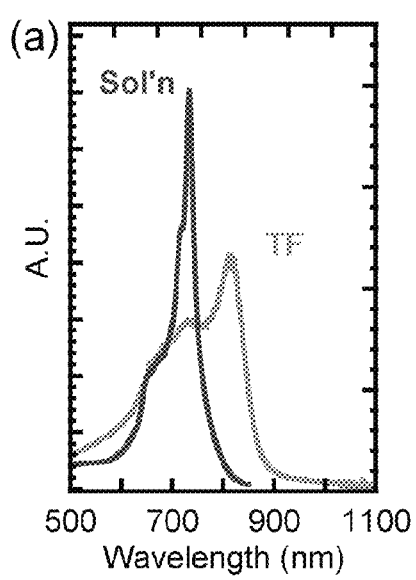
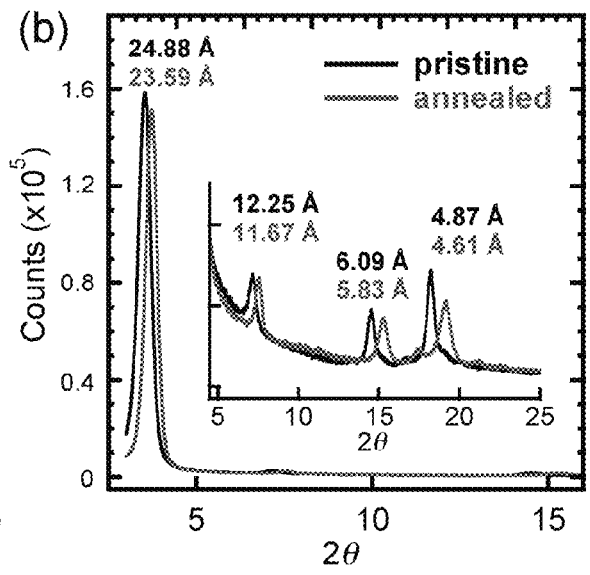
Figure 3A  Figure 3B
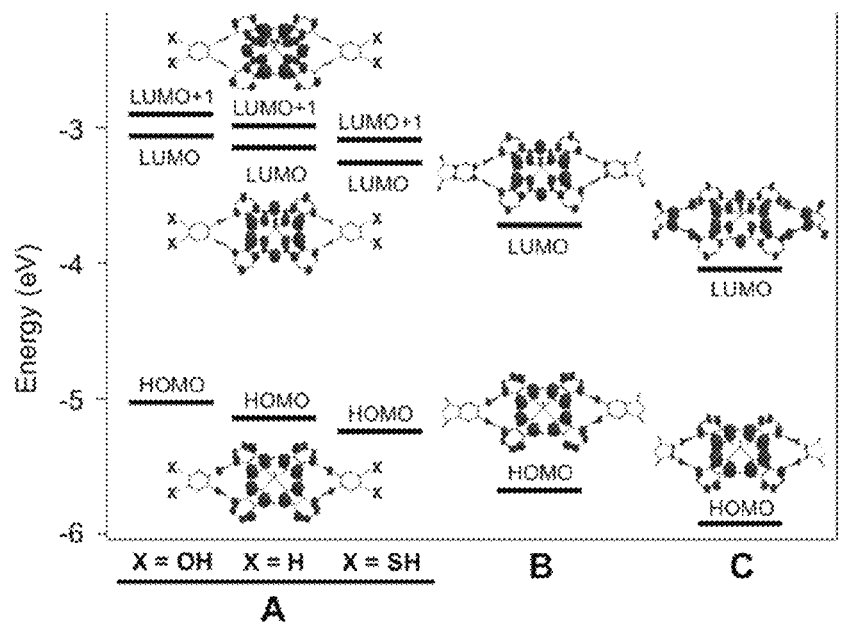
Figure 5

CONJUGATED SIDE-STRAPPED PHTHALOCYANINES AND METHODS FOR PRODUCING AND USING THE SAME

CROSS-REFERENCE TO RELATED APPLICATIONS

This application claims the priority benefit of U.S. Provisional Application No. 61/972,230, filed Mar. 29, 2014, which is incorporated herein by reference in its entirety.

STATEMENT REGARDING FEDERALLY FUNDED RESEARCH

This invention was made with government support under Grant No. DE-SC0001084 awarded by DOE. The government has certain rights in the invention.

FIELD OF THE INVENTION

The present invention relates to conjugated side-strapped phthalocyanines and methods for producing and using the same. In one particular embodiment, conjugated side-strapped phthalocyanines of the invention are used in electronic devices such as p-type or n-type organic semiconductors.

BACKGROUND OF THE INVENTION

Phthalocyanines (Pcs) are promising organic semiconductors that can achieve high hole mobility due to their tight π-π stacking Modification with solubilizing groups increases their solubility in common organic solvents to enable purification, characterization and solvent processing. Unfortunately, however, the solubilizing substituents (usually electronically inert) tend to interfere with π-π stacking and thus significantly reduce hole mobility.

Therefore, there is a need for phthalocyanines that retain a relatively high hole mobility while also having a relatively high solubility in organic solvents to provide ease of fabrication.

SUMMARY OF THE INVENTION

Many phthalocyanines (Pcs) are used as the electron donating layer material in organic photovoltaic devices (OPV). The mobility of free charge carrier (hole) within this layer greatly influences the overall efficiency of OPV. Some aspects of the invention provide phthalocyanines that can be readily produced, have a relative high hole mobility, and are solution processable. The present invention also provides a method for producing such phthalocyanines as well as electronic devices and compositions comprising such phthalocyanines.

Some of the compounds of the invention can be readily prepared. For example, in one aspect of the invention, a method is provided for producing a conjugated side-strapped phthalocyanine compound of the formula:

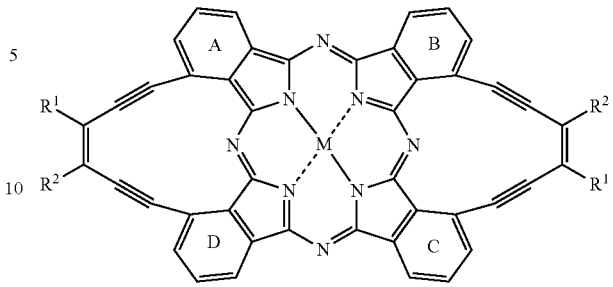

said method comprising:
  contacting a compound of the formula:

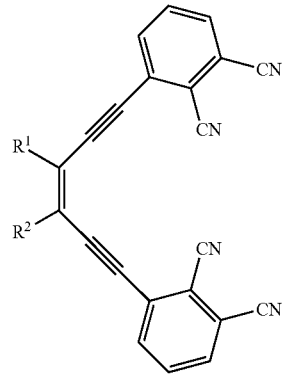

with a metal salt in the presence of a base under conditions sufficient to produce the conjugated side-strapped phthalocyanine compound of Formula II.
wherein
  M is a phthalocyanine coordinating moiety derived from said metal salt; and
  each of $R^1$ and $R^2$ is independently hydrogen, $C_1$-$C_{25}$ alkyl and $C_1$-$C_{25}$ haloalkyl;
  or $R^1$ and $R^2$ together with the carbon atom to which they are attached to form aryl, heteroaryl, or heterocyclyl ring structure, each of which is optionally substituted.

Suitable bases include relatively non-nucleophilic bases including organic amine compounds such as 1,8-diazabicyclo[5.4.0]undec-7-ene (DBU), triethylamine, diisopropylamine, alkylated diisopropylamine, and the like.

Suitable solvents for the reaction include tetrahydrofuran, ether, dimethylformamide, alcohols (such as isopropanol, pentanol, butanol, etc.), carbon tretrachloride, toluene, xylene, and the like, as well as mixtures thereof.

BRIEF DESCRIPTION OF THE DRAWINGS

FIG. 3A is a UV-Vis absorption spectra of thin-film of compound 1 in contrast with the solution spectrum showing the expected enhanced near-IR absorption in the condensed phase.

FIG. 3B is an XRD of a drop cast thin film of 1 on Si before and after annealing (100° C., 30 min.).

FIG. 5 is a graph of frontier molecular orbital energies for scaffolds A-C (FIG. 7) computed at the B3LYP/6-31G* level. A significant increase in IP was observed across the series, modulated by side-chain substituents in A and the imide moiety in B and C.

DETAILED DESCRIPTION OF THE INVENTION

Figure 1:
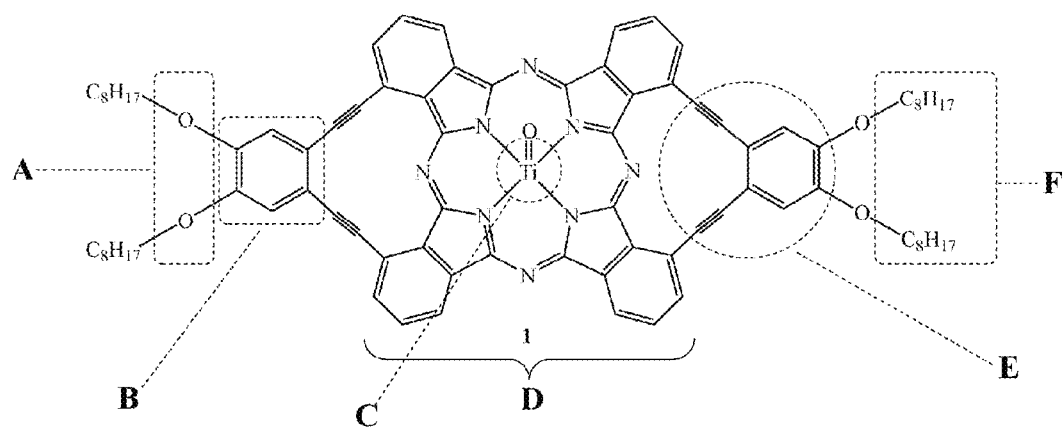
FIG. 1 shows one example (Compound 1) of a rigid "side-strapped" trans-$A_2B_2$ Pc scaffold.

Significant progress has been made in improving the efficiency of both planar heterojunction (PHJ) and bulk heterojunction (BHJ) organic solar cells (i.e., organic photovoltaics or OPVs). Currently, 7-12% power conversion efficiency (PCE) research cells are possible with both polymer and small molecule active layers. However, some of the challenges remaining to achieve high OPVs efficiencies, at the module level, include, but are not limited to, (i) extending the spectral response of the OPV to the near-IR, taking advantage of the full AM1.5 solar irradiance. To this end, lower bandgap polymers have been recently introduced, but there are physical limits in terms of their stability which may prevent a spectral response extending out to ca. 1000 nm. Full capture of the entire AM1.5G spectrum will require new classes of light absorbing dyes, incorporated into single junction OPVs, or into tandem architectures (TOPVs) where the near-IR response of one sub-cell complements the visible response of the adjacent sub-cell; (ii) achieving this near-IR response while keeping the open-circuit photopotential ($V_{OC}$) high (e.g., >0.7 volts). Differences in ionization potential (IP) and electron affinity (EA) of the donor and acceptor phases respectively control $V_{OC}$ and must be kept high, and energetically homogenous active layers and contacts must be created to avoid the recombination processes which further limit both $V_{OC}$ and short-circuit photocurrents ($J_{SC}$); (iii) creating the highest possible donor/acceptor interfacial area, to provide for high short-circuit photocurrent ($J_{SC}$), while achieving "vectorial charge transfer pathways" in the active layer; (iv) creating selective interlayers at the contacting electrodes that provide for selective hole harvesting at the cathode and electron-harvesting at the anode; and (v) minimizing series ($R_S$) and maximizing shunt ($R_P$) parasitic resistances, and minimizing dark injection, especially into trap states—these factors typically arise from low charge mobilities, poor interfacial wetting and poor control of film morphology, and all effects negatively impact power conversion efficiencies ($\eta$).

Bulk-heterojunction (BHJ) organic solar cells have shown the highest efficiencies to date, using either single donor (D)/acceptor (A) heterojunction, or tandem OPVs with two spectrally complementary DA pairs. Extending their response to the near-IR, without a significant loss of $V_{OC}$ is challenging. Small molecule-based OPVs, using either crystalline, vacuum deposited dyes, or soluble small molecules, have recently shown improved efficiencies. The recent studies on DTS(PTTh$_2$)$_2$/PC$_{70}$BM OPVs with PCEs of now approaching 9% show that efficient OPVs are possible using small molecule donors and acceptors, with molecular architectures that ensure good charge mobilities in both the donor and acceptor domains. The optical bandgap of these small molecule BHJ ("SMBHJ") materials, however, is approximately 1.5 eV based on the absorption onset of the thin film (l=815 nm). Therefore, new active materials are needed that significantly convert light to electrical energy beyond 800 nm.

Some aspects of the present invention provide conjugated side-strapped phthalocyanine compounds that can convert light to electrical energy in a significant amount. In some embodiments, compounds of the invention can also convert light to electrical energy beyond 800 nm. As used herein "phthalocyanine compound" refers to a compound having phthalocyanine as its core chemical structure, i.e., a compound having the following core structural formula:

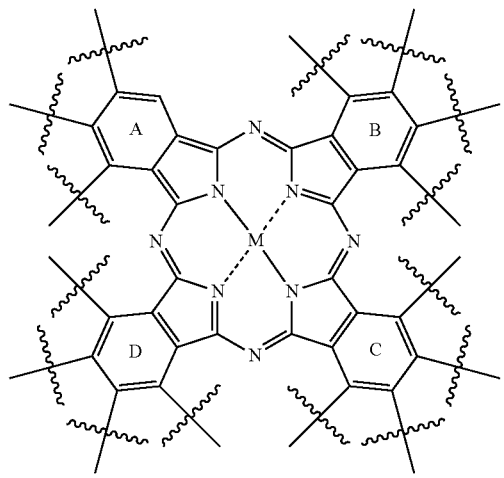

where M is a metal or hydrogen. It should be appreciated that when M is hydrogen, two of the nitrogen atoms (i.e., ones in "A" and "C" rings) each have a separate hydrogen atom. It should be noted that unless explicitly stated or context requires otherwise, the term "phthalocyanine compound" also includes nathphalocyanine ("Nc") compound in which the phenyl rings A, B, C and D are replaced with naphthyl rings. In some embodiments, compounds of the invention have 2-fold symmetry. The term "conjugated side-strapped phthalocyanine compound" refers to a phthalocyanine compound as disclosed herein that includes substituents whose π-electron system is conjugated with the π-electronic system of the core phthalocyanine moiety and links two adjacent phenyl rings (e.g., A with B, and/or B with C, and/or C with D and/or D with A, etc.) within the core phthalocyanine moiety.

Several recent studies have shown that the wavelength response of BHJ and PHJ OPVs can be extended to the near-IR through the addition of small molecules, however, the OPV efficiencies have been disappointing. Good near-IR responses have been obtained for photoconductors (but not OPVs) using "porphyrin tape" donors and $C_{60}$ as an acceptor. Without being bound by any theory, it is believed that chromophore self-organization is critical, provided that design provides for optimal aggregation, for high hole/electron mobilities in the condensed phase. Condensed phase molecular architectures in small molecules that provide for extensive near-IR (700-1400 nm) absorbance are also predicted to provide high charge mobilities, a virtue of many semiconducting polymers, not often seen in small molecules.

Titanyl phthalocyanine (TiOPc) is one of several non-planar tri- and tetravalent Pcs, such as ClAlPc and ClInPc, that can show extensively red-shifted thin-film Q-band spectra. It would provide an excellent platform for small molecule active materials with extended near-IR response and high charge mobility, and has only recently has been explored in OPVs. It is believed that TiOPc's condensed phase photoconductivity and near-IR absorptivity results from the non-planarity and dipolar character of the chromophore, which also leads to several known crystalline polymorphs (e.g., amorphous TiOPc, Phase I, Phase II, and the Y Phase) some of which significantly extend the Q-band absorbance well into the near-IR region and significantly improve its photoelectrical activity. It has been shown that the transition from the Phase I (monoclinic) to the Phase II (triclinic) polymorph is accentuated by solvent or thermal annealing, resulting in shortening of one of the unit cell dimensions and providing the close contact and energetic distortion of the π-electrons in adjacent macrocycles that leads to an absorbance maximum at 830 nm with an optical bandgap approaching 1.3 eV (950 nm). This represents a significant extension of photon harvesting capacity. Similar changes in absorptivity have been achieved in synthetically sophisticated porphyrin systems, through covalent linking of adjacent units, and formation of "tapes." The electronic properties of many different discotic molecular systems have recently been enhanced through the formation of "nanowires" often wider than the individual molecular diameter, but with a relatively long longitudinal coherence (e.g., hundreds of nanometers) and a significantly enhanced electrical properties.

Phase-II TiOPc also has a higher probability for exciton dissociation and higher charge (hole) mobilities necessary for increased OPV efficiency due to the relatively short intermolecular distances between adjacent TiOPc molecules observed in both convex and concave pairs of the triclinic unit cell. Theoretical models and photoconductivity studies with TiOPc predict that enhanced exciton diffusion lengths and charge mobilities occur in staggered cofacial geometries of Pc/Nc aggregates in general. An additional advantage demonstrated by the tri- and tetravalent Pcs is their high ionization potential, which, associated with $C_{60}$ as an electron acceptor, has led to OPVs with $V_{OC}$ close to 0.8 volts, even for the polymorphs which show strong near-IR absorptivity. Provided that such chromophore coherence can be achieved in inexpensive, synthetically tractable, solution-processable Pcs and Ncs, good near-IR photoactivity with good associated charge mobilities can be expected when such dyes are used as donor components in BHJ OPVs with electron acceptors such as fullerenes.

Crystalline TiOPc, however, is particularly insoluble necessitating relatively expensive and inherently low-throughput vapor deposition techniques to produce near-IR absorbing thin-films for incorporation into devices such as OPVs, precluding its incorporation into solution-processed devices. And while successful efforts have been made to obtain specific TiOPc polymorphs by varying vapor deposition processing conditions, success at polymorph control has not been obtained with soluble versions of TiOPc—all prior efforts towards obtaining near-IR absorbing polymorphs in solution-processed thin films of TiOPc derivatives have not produced the desired near-IR absorbing phases. This lack of control in obtaining the desired polymorphs in thin-films of soluble TiOPc derivatives severely limits use of these materials as active materials in solution processed OPVs and in related molecular electronic device platforms.

Phthalocyanine compounds of the invention are useful as OPVs with good near-IR responsivity, and high $V_{OC}$. Some phthalocyanine compounds of the invention comprise the phthalocyanine core structure, as described above, which is complexed to TiO or other metal complexing agents (typically tri- or tetravalent metals). Phthalocyanine compounds of the invention are based on a rigid, conjugated side-strapped Pc cores that incorporate several modular design elements.

Studies using phthalocyanine compounds of the invention show that absorption into the near-IR can be extended while maintaining the overlap of the Pc cores seen in crystalline TiOPc. These strong dipolar interactions can be exploited while providing the coherent long range aggregation that leads to high charge mobilities in the bulk phase (Class I materials, Type I OPV platforms), or nanometer-scale control over their placement at the interface between polymer donor (host) domains and small molecule fullerene acceptor (Class II materials, Type II OPV platforms). Class I and II materials require solubilizing groups in two of the four Pc quadrants with peripheral groups that provide (a) for processing into near-IR absorbing active layers (Type I); or (b) for their selective placement at donor host polymer/acceptor interfaces (ternary Type II OPVs). For Class I or II materials peripheral groups (i.e., substituents on the phenyl rings A, B, C and/or D) placed in opposed quadrants afford the overlap of the non-functionalized rings in adjacent Pc cores, mimicking the overlap in crystalline Phase II TiOPc.

It has been found by the present inventors that use of conjugated side-strapped phthalocyanine compounds of the invention results in aggregates with good near-IR absorptivity, and with molecular architectures with good dispersibility and good charge (hole) mobilities in the microscopic domains. Such properties are needed to ensure efficient photocurrent production (Type I), or nanometer-scale control over their placement at the interface between (host) donor domains and fullerene acceptor domains (Type II). The conjugated side-strapped phthalocyanine compounds of the invention provide control of the molecular overlap known to be important to near-IR spectral response and photoactivity while simultaneously providing for nanoscale mixing of the compound of the invention as a donor with fullerene acceptors (Class I dyes), and/or placement of the compound of the invention aggregated at a donor polymer/electron acceptor interface (Class II dyes), without loss of the intermolecular interactions in the host polymer or fullerene domains which are believed to be important for maintaining high charge mobilities and high open-circuit photovoltages ($V_{OC}$). The compounds of the invention provide a new approach to combining the high absorptivities and photochemical stability with a molecular structure that sustains solution processability and provides routes to "tape-like" aggregates with the high charge mobilities attributed to "staggered" Pc-Pc architectures.

Figure 2:
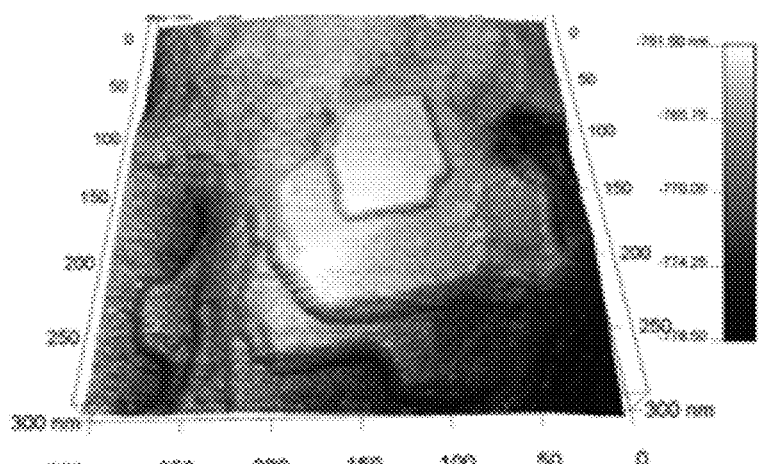
FIG. 2 is an AFM image of drop cast film on HOPG of specific example of dye 1 (i.e., compound 1) of the invention (where M=TiO, R=$OC_8H_{17}$), demonstrating the layered growth predicted from this material, with layer plane thickness of ca. 2.5 nm. X-ray thin film diffraction (see FIG. 3B) data show monoclinic unit cells, two molecules per cell, with c-axis dimensions comparable to that indicated in the AFM data.

Compounds of the invention can be used, for example, in the creation of unique light absorbing molecular semiconductors, designed to enable two new types of solution processable organic solar cells (OPVs) with extended near-IR response and high open-circuit photovoltages ($V_{OC}$). Type I platforms combine electron donor dyes (soluble metal phthalocyanine compounds of the invention) with small molecule electron acceptors (two component OPVs). Type II platforms combine variants of these dyes as "guest dopants" in mixtures of small molecule electron acceptors and semiconducting host polymers (three component OPVs with "cascaded" energy levels, FIG. 2). Binary planar (PHJ) and bulk (BHJ) heterojunction OPVs (Type I) can be created using compounds of the invention and fullerene acceptors, enabling correlation of the offsets in frontier orbital energies which determine $V_{OC}$ and photocurrent production ($J_{SC}$), with OPV performance. Ternary heterojunctions (Type II) are designed to produce energy and charge transport "cascades" (energy transfer from host polymer or electron acceptor→guest dye, plus vectorial electron and hole transport in all phases).

In one aspect of the invention, a conjugated side-strapped phthalocyanine compound of the invention is of the formula:

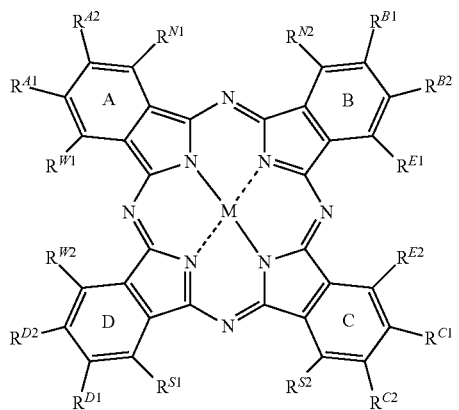

I wherein
M is a phthalocyanine coordinating moiety
at least one pair of $R^{W1}$ and $R^{W2}$, or $R^{N1}$ and $R^{N2}$, or $R^{E1}$ and $R^{E2}$, or $R^{S1}$ and $R^{S2}$ form a conjugated side-strapped substituent and the remaining are independently selected from the group consisting of:
(i) H;
(ii) $C_1$-$C_{25}$ alkyl;
(iii) a moiety of the formula: —$(CH_2CH_2O)_a$—$(CH_2)_bOR_{a1}$, —$(CH_2CH_2O)_a$—$(CH_2)_bNR_{a2}R_{a3}$, —$(CH_2CH_2O)_a$—$(CH_2)_bCONR_{a2}R_{a3}$, —$(CH_2CH_2O)_a$—$(CH_2)_bCN$, —$(CH_2CH_2O)_a$—$(CH_2)_bCl$, —$(CH_2CH_2O)_a$—$(CH_2)_bBr$, —$(CH_2CH_2O)_a$—$(CH_2)_bI$, —$(CH_2CH_2O)_a$—$(CH_2)_b$-Phenyl, or —$(CH_2CH_2O)_a$—$(CH_2)_b$-ethynyl;
(iv) an aryl or a heteroaryl group of the formula

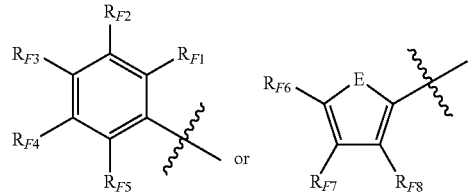

wherein E is S, O, or NH, and $R_{F1}$, $R_{F2}$, $R_{F3}$, $R_{F4}$, $R_{F5}$, $R_{F6}$, $R_{F7}$, and $R_{F8}$ are independently selected from the group consisting of:
(a) H;
(b) $C_1$-$C_{25}$ alkyl;
(c) a moiety of the formula: —$(CH_2CH_2O)_a$—$(CH_2)_bOR_{a1}$, —$(CH_2CH_2O)_a$—$(CH_2)_bNR_{a2}R_{a3}$, —$(CH_2CH_2O)_a$—$(CH_2)_bCONR_{a2}R_{a3}$, —$(CH_2CH_2O)_a$—$(CH_2)_bCN$, —$(CH_2CH_2O)_a$—$(CH_2)_bCl$, —$(CH_2CH_2O)_a$—$(CH_2)_bBr$, —$(CH_2CH_2O)_a$—$(CH_2)_bI$, —$(CH_2CH_2O)_a$—$(CH_2)_b$-Phenyl, or —$(CH_2CH_2O)_a$—$(CH_2)_b$-ethynyl;
(d) —$NR_{e1}R_{e2}$, —$OR_{e3}$, and —$SR_{e4}$;
(e) an aryl or heteroaryl group; and
(f) a polymerizable group;
(v) a fused aromatic ring of the formula:

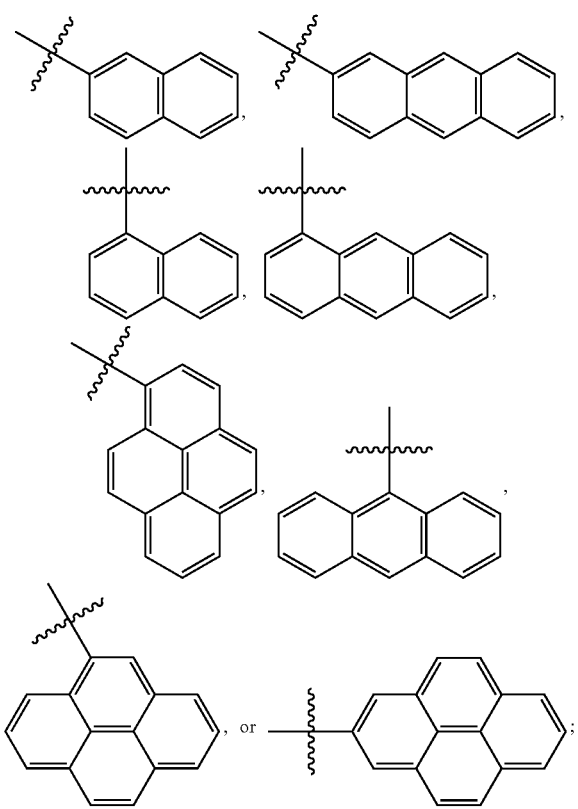

(vi) a polymerizable group selected from the group consisting of vinyl, allyl, 4-styryl, acryloyl, methacroyl, epoxide, acrylonitrile, isocyanate, isothiocyanate, strained ring olefins; —(CH$_2$)$_d$SiCl$_3$, —(CH$_2$)$_d$Si(OCH$_2$CH$_3$)$_3$, and —(CH$_2$)$_d$Si(OCH$_3$)$_3$;

(vii) halide; and (viii) —NR$_{e1}$R$_{e2}$, —OR$_{e3}$, or —R$_{e4}$;

each of R$^{A1}$, R$^{A2}$, R$^{B1}$, R$^{B2}$, R$^{C1}$, R$^{C2}$, R$^{D1}$ and R$^{D2}$ is independently selected from the group consisting of:

(i) H;

(ii) C$_1$-C$_{25}$ alkyl;

(iii) a moiety of the formula: —(CH$_2$CH$_2$O)$_a$—(CH$_2$)$_b$OR$_{a1}$, —(CH$_2$CH$_2$O)$_a$—(CH$_2$)$_b$NR$_{a2}$R$_{a3}$, —(CH$_2$CH$_2$O)$_a$—(CH$_2$)$_b$CONR$_{a2}$R$_{a3}$, —(CH$_2$CH$_2$O)$_a$—(CH$_2$)$_b$CN, —(CH$_2$CH$_2$O)$_a$—(CH$_2$)$_b$Cl, —(CH$_2$CH$_2$O)$_a$—(CH$_2$)$_b$Br, —(CH$_2$CH$_2$O)$_a$—(CH$_2$)$_b$I, —(CH$_2$CH$_2$O)$_a$—(CH$_2$)$_b$-Phenyl, —(CH$_2$CH$_2$O)$_a$—(CH$_2$)$_b$-ethynyl;

(iv) an aryl or heteroaryl group of the formula

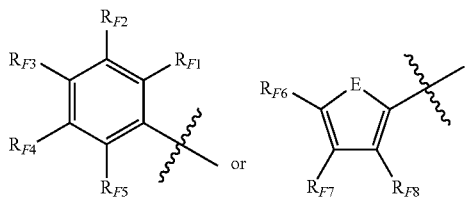

wherein E is S, O, or NH, and R$_{F1}$, R$_{F2}$, R$_{F3}$, R$_{F4}$, R$_{F5}$, R$_{F6}$, R$_{F7}$, and R$_{F8}$ are independently selected from the group consisting of:

(a) H;

(b) C$_1$-C$_{25}$ alkyl;

(c) a moiety of the formula: —(CH$_2$CH$_2$O)$_a$—(CH$_2$)$_b$OR$_{a1}$, —(CH$_2$CH$_2$O)$_a$—(CH$_2$)$_b$NR$_{a2}$R$_{a3}$, —(CH$_2$CH$_2$O)$_a$—(CH$_2$)$_b$CONR$_{a2}$R$_{a3}$, —(CH$_2$CH$_2$O)$_a$—(CH$_2$)$_b$CN, —(CH$_2$CH$_2$O)$_a$—(CH$_2$)$_b$Cl, —(CH$_2$CH$_2$O)$_a$—(CH$_2$)$_b$Br, —(CH$_2$CH$_2$O)$_a$—(CH$_2$)$_b$I, —(CH$_2$CH$_2$O)$_a$—(CH$_2$)$_b$-Phenyl, or —(CH$_2$CH$_2$O)$_a$—(CH$_2$)$_b$-ethynyl;

(d) —NR$_{e1}$R$_{e2}$, —OR$_{e3}$, and —SR$_{e4}$;

(e) an aryl or heteroaryl group; and (f) a polymerizable group;

(v) a fused aromatic ring of the formula:

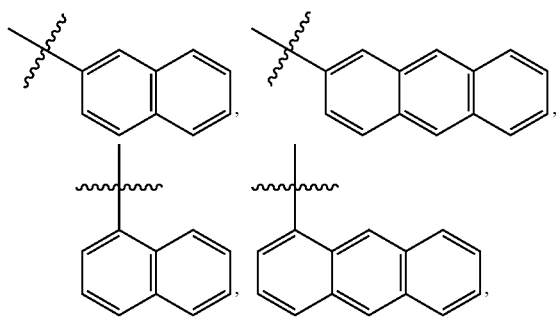

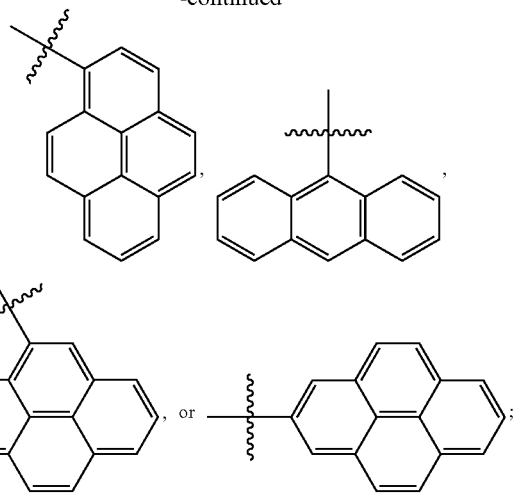

(vi) a polymerizable group selected from the group consisting of vinyl, allyl, 4-styryl, acryloyl, methacroyl, epoxide, acrylonitrile, isocyanate, isothiocyanate, strained ring olefins; —(CH$_2$)$_d$SiCl$_3$, —(CH$_2$)$_d$Si(OCH$_2$CH$_3$)$_3$, and —(CH$_2$)$_d$Si(OCH$_3$)$_3$;

(vii) halide;

(viii) —NR$_{e1}$R$_{e2}$, —OR$_{e3}$, or —SR$_{e4}$;

or each pair of R$^{A1}$ and R$^{A2}$, R$^{B1}$ and R$^{B2}$, R$^{C1}$ and R$^{C2}$, and R$^{D1}$ and R$^{D2}$ along with the carbon atom to which they are attached to form an optionally substituted phenyl ring moiety;

a is an integer from 0 to 10;

b is an integer from 1 to 25;

d is an integer between 0 and 25;

each of R$_{e1}$, R$_{e2}$, R$_{e3}$, and R$_{e4}$ is independently selected from the group consisting of:

(a) H;

(b) C$_1$-C$_{25}$ alkyl;

(c) a moiety of the formula: —(CH$_2$CH$_2$O)$_a$—(CH$_2$)$_b$OR$_{a1}$, —(CH$_2$CH$_2$O)$_a$—(CH$_2$)$_b$NR$_{a2}$R$_{a3}$, —(CH$_2$CH$_2$O)$_a$—(CH$_2$)$_b$CONR$_{a2}$R$_{a3}$, —(CH$_2$CH$_2$O)$_a$—(CH$_2$)$_b$CN, —(CH$_2$CH$_2$O)$_a$—(CH$_2$)$_b$Cl, —(CH$_2$CH$_2$O)$_a$—(CH$_2$)$_b$Br, —(CH$_2$CH$_2$O)$_a$—(CH$_2$)$_b$I, —(CH$_2$CH$_2$O)$_a$—(CH$_2$)$_b$-Phenyl, or —(CH$_2$CH$_2$O)$_a$—(CH$_2$)$_b$-ethynyl;

(d) an aryl or heteroaryl group; and (e) a polymerizable group; and each of R$_{a1}$, R$_{a2}$, and R$_{a3}$ is independently selected from the group consisting of H, C$_1$-C$_{25}$ alkyl and aryl.

The term "conjugated side-strapped substituent" refers to a moiety whose π-electron system is conjugated with the π-electronic system of the core phthalocyanine moiety and links two phenyl rings within the core phthalocyanine moiety; thus, forming in many instances a relatively rigid structure. The term "alkyl" refers to a saturated linear hydrocarbon moiety of one to twenty five, typically one to twelve, and often one to eight carbon atoms or a saturated branched hydrocarbon moiety of three to twenty five, typically three to twelve, and often three to eight carbon atoms. Exemplary alkyl group include, but are not limited to, methyl, ethyl, n-propyl, 2-propyl, tert-butyl, pentyl, and the like. The term "aryl" refers to a mono-, bi-, tri-, tetra-, or pentacyclic aromatic hydrocarbon moiety of 6 to 30 ring atoms which is optionally substituted with one or more, typically one, two, or three substituents within the ring structure. When two or more substituents are present in an aryl group, each substituent is independently selected. The term "fused aryl" group is a subset of aryl group in which two or more aromatic rings are fused together. The term "polymerizable group" refers to vinyl, allyl, 4-styryl, acryloyl, methacroyl, epoxide (such as cyclohexene oxide), acrylonitrile, which may be polymerized by either a radical, cationic, or anionic polymerization; isocyanate, isothiocyanate, epoxides such that the polymerizable functionality may be copolymerized with difunctional amines or alcohols such as $HO(CH_2)_gOH$, $H_2N(CH_2)_gNH_2$, where g is an integer between 1 and 25; strained ring olefins such as dicyclopentadienyl, norbornenyl, and cyclobutenyl where the chromophore (i.e., phthalocyanine core moiety) is attached to any of the saturated carbon linkages in the strained ring olefins—the monomer may be polymerized via ring opening metathesis polymerization using an appropriate metal catalyst as is known in the art; and $—(CH_2)_dSiCl_3$, $—(CH_2)_dSi(OCH_2CH_3)_3$, or $—(CH_2)_dSi(OCH_3)_3$ where d is an integer from 1 to 25—the monomers can be reacted with water either under conditions known to those skilled in the art to form either thin film or monolithic organically modified sol-gel glasses, or modified silicate surfaces. The terms "halo," "halogen" and "halide" are used interchangeably herein and refer to fluoro, chloro, bromo, or iodo. The term "heteroaryl" means a monocyclic or bicyclic aromatic moiety of 5 to 12 ring atoms containing one, two, or three ring heteroatoms selected from N, O, or S, the remaining ring atoms being C. The term heteroaryl includes, but is not limited to, pyridyl, furanyl, thiophenyl, thiazolyl, isothiazolyl, triazolyl, imidazolyl, isoxazolyl, pyrrolyl, pyrazolyl, pyrimidinyl, benzofuranyl, isobenzofuranyl, benzothiazolyl, benzoisothiazolyl, benzotriazolyl, indolyl, isoindolyl, benzoxazolyl, quinolyl, isoquinolyl, benzimidazolyl, benzisoxazolyl, benzothiophenyl, dibenzofuran, and benzodiazepin-2-one-5-yl, and the like.

In one particular embodiment, the conjugated side-strapped substituent is a moiety of the formula:

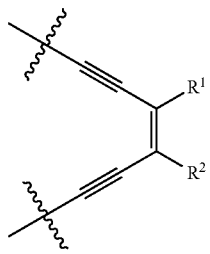

wherein
each of $R^1$ and $R^2$ is independently selected from the group consisting of:
(a) H;
(b) $C_1$-$C_{25}$ alkyl;
(c) a moiety of the formula: $—(CH_2CH_2O)_a—(CH_2)_bOR_{a1}$, $—(CH_2CH_2O)_a—(CH_2)_bNR_{a2}R_{a3}$, $—(CH_2CH_2O)_a—(CH_2)_bCONR_{a2}R_{a3}$, $—(CH_2CH_2O)_a—(CH_2)_bCN$, $—(CH_2CH_2O)_a—(CH_2)_bCl$, $—(CH_2CH_2O)_a—(CH_2)_bBr$, $—(CH_2CH_2O)_a—(CH_2)_bI$, $—(CH_2CH_2O)_a—(CH_2)_b$-Phenyl, $—(CH_2CH_2O)_a—(CH_2)_b$-ethynyl, wherein $0 \le a \le 10$ and $1 \le b \le 25$ and $R_{a1}$, $R_{a2}$, and $R_{a3}$ are independently selected from the group consisting of H, $C_1$-$C_{25}$ alkyl and aryl;
(d) $—NR_{e1}R_{e2}$, $—OR_{e3}$, and $—SR_{e4}$, wherein $R_{e1}$, $R_{e2}$, $R_{e3}$, and $R_{e4}$ are independently selected from the group consisting of H, $C_1$-$C_{25}$ alkyl, and phenyl;
(e) an aryl or heteroaryl group; and
(f) a polymerizable group; or
$R^1$ and $R^2$ together with the carbon atoms to which they are attached to form an aryl or a heteroaryl, each of which is optionally substituted.

Within these embodiments, in some instances, $R^1$ and $R^2$ together with the carbon atoms to which they are attached to form an optionally substituted phenyl. As used herein, the term "optionally substituted" means a moiety (e.g., phenyl ring) that may or may not be substituted. When the aryl or heteroaryl is substituted, it typically has one or more substituents, typically one, two or three substituents. In some cases, $R^1$ and $R^2$ together with the carbon atoms to which they are attached to form a phenyl group that is substituted with at least one substituent selected from the group consisting of:
(a) $C_1$-$C_{25}$ alkyl;
(b) a moiety of the formula: $—(CH_2CH_2O)_a—(CH_2)_bOR_{a1}$, $—(CH_2CH_2O)_a—(CH_2)_bNR_{a2}R_{a3}$, $—(CH_2CH_2O)_a—(CH_2)_bCONR_{a2}R_{a3}$, $—(CH_2CH_2O)_a—(CH_2)_bCN$, $—(CH_2CH_2O)_a—(CH_2)_bCl$, $—(CH_2CH_2O)_a—(CH_2)_bBr$, $—(CH_2CH_2O)_a—(CH_2)_bI$, $—(CH_2CH_2O)_a—(CH_2)_b$-Phenyl, $—(CH_2CH_2O)_a—(CH_2)_b$-ethynyl, wherein a is an integer from 0 to 10, b is an integer from 1 to 25 and $R_{a1}$, $R_{a2}$, and $R_{a3}$ are independently selected from the group consisting of H, $C_1$-$C_{25}$ alkyl and aryl;
(c) $—NR_{e1}R_{e2}$, $—OR_{e3}$, and $—SR_{e4}$, wherein $R_{e1}$, $R_{e2}$, $R_{e3}$, and $R_{e4}$ are independently selected from the group consisting of H, $C_1$-$C_{25}$ alkyl, and phenyl;
(d) an aryl or heteroaryl group; and
(e) a polymerizable group.

Typically, $R^1$ and $R^2$ is independently hydrogen, $C_1$-$C_{25}$ alkyl and $C_1$-$C_{25}$ haloalkyl; or $R^{x1}$ and $R^{x2}$ together with the carbon atom to which they are attached to form aryl, heteroaryl, or heterocyclyl ring structure, each of which is optionally substituted.

Some of the specific conjugated side-strapped phthalocyanine compounds of the invention include, but are not limited to, compounds of the formulas:

IA

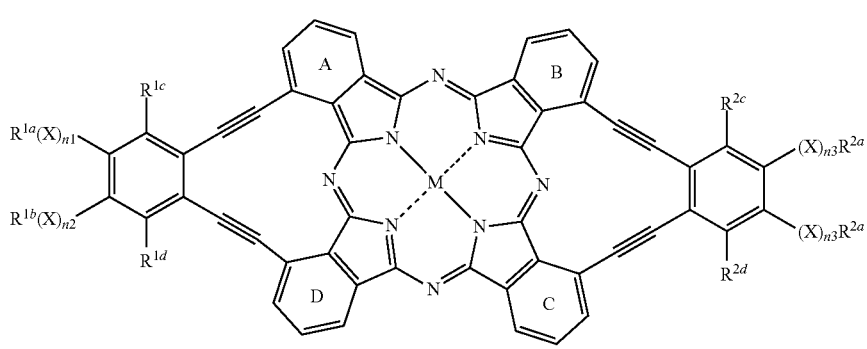

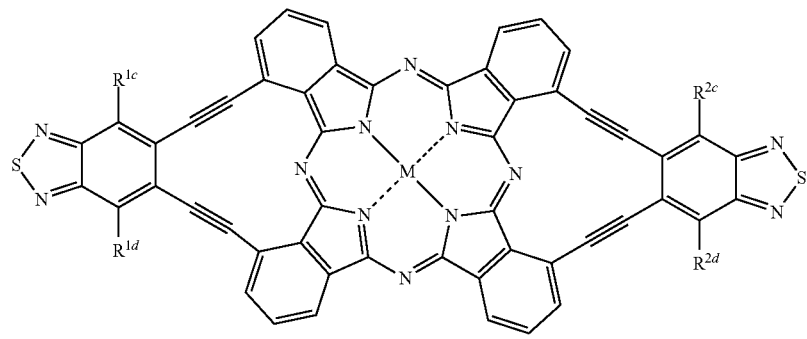

IB

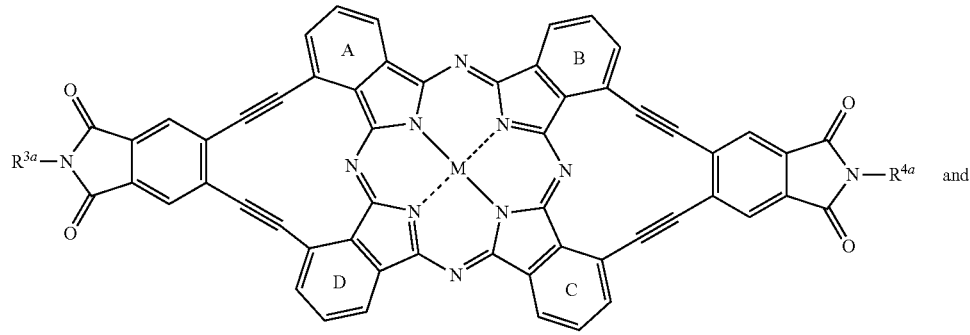

IC

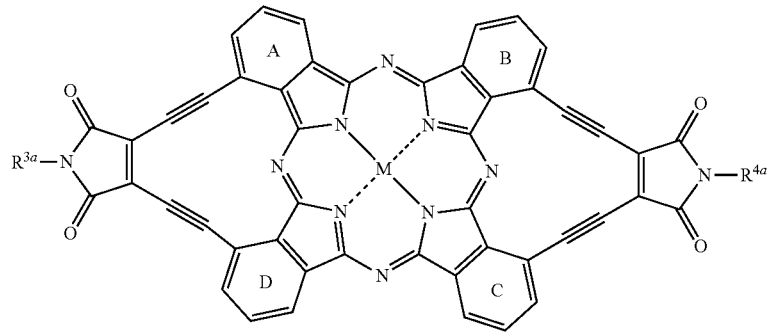

ID where
- M, $R^{N1}$, $R^{N2}$, $R^{S1}$, $R^{S2}$, $R^{A1}$, $R^{A2}$, $R^{B1}$, $R^{B2}$, $R^{C1}$, $R^{C2}$, $R^{D1}$ and $R^{D2}$ are those defined herein;
- each of $R^{1a}$, $R^{1b}$, $R^{1c}$, $R^{1d}$, $R^{2a}$, $R^{2b}$, $R^{2c}$, $R^{2d}$, $R^{3a}$ and $R^{4a}$ is independently selected from the group consisting of hydrogen, $C_1$-$C_{25}$ alkyl and $C_1$-$C_{25}$ haloalkyl;
- each n is independently 0 or 1; and
- X is O or S.

In some embodiments, M comprises a metal selected from the group consisting of vanadium, indium, gallium, aluminum, titanium, tin, lead, bismuth, manganese, and phosphorus.

Other aspects of the invention provide a composition comprising a conjugated side-strapped phthalocyanine compound that is solution processable. In one embodiment, the conjugated side-strapped phthalocyanine compounds of the invention have a 2-fold symmetry. Yet in other embodiments, the conjugated side-strapped phthalocyanine compounds of the invention have a solubility in tetrahydrofuran (THF) of at least about 0.5 mole/L, typically at least about 1 mole/L, and often at least 5 mole/L. The term "about" refers to ±20%, typically ±10%, and often ±5% of the numeric value. Still in other embodiments, the conjugated side-strapped phthalocyanine compounds of the invention have a solubility in chloroform of at least about 0.5 mole/L, typically at least about 1 mole/L, and often at least 5 mole/L. In other embodiments, the conjugated side-strapped phthalocyanine compounds of the invention have a solubility in pyridine of at least about 0.5 mole/L, typically at least about 1 mole/L, and often at least 5 mole/L.

Such a relatively high solvent solubility allows the conjugated side-strapped phthalocyanine compounds of the invention to be used in a wide variety of electronic devices. In particular, a thin film of conjugated side-strapped phthalocyanine compounds of the invention can be used in an electronic devices such as, but not limited to, an optoelectronic device, a photovoltaic, a semi-conductor, a solar cell, a field-effect transistor, organic light emitting diode, as well as other electronic devices that utilize a hole mobility.

In some embodiments, the hole mobility within a thin film produced from the conjugated side-strapped phthalocyanine compounds of the invention is at least about 0.10 $cm^2V^{-1}s^{-1}$, typically at least about 0.50 $cm^2V^{-1}s^{-1}$, often at least about 0.90 $cm^2V^{-1}s^{-1}$, and most often at least about 0.95 $cm^2V^{-1}s^{-1}$.

Yet in other embodiments, a thin film produced from the conjugated side-strapped phthalocyanine compounds of the invention comprises ABAB stacking.

The present invention also provides methods for producing and using the same. In addition, the invention also provides various electronic devices and/or components that comprise a conjugated side-strapped phthalocyanine compound of the invention. While a variety of synthetic methods can be used to produce conjugated side-strapped phthalocyanine compounds of the invention, one particular embodiment utilizes cyclization of alkyne bridged bisphthalonitriles, which were prepared through Sonogashira coupling reactions. Thin film of Pcs can be produced on highly ordered pyrolytic graphite (HOPG), which can be readily monitored using atomic force microscopy ("AFM"). In some embodiments, the conjugated side-strapped phthalocyanine compounds of the invention result in an ordered "plate-like" architecture of thin film on HOPG. In studies using conductive-AFM showed that a mobility (i.e., electron or hole mobility) within a thin film that is produced using the conjugated side-strapped phthalocyanine compounds of the invention is in the level as disclosed herein.

In some embodiments, M is a metal or a semi-metal coordinating complex. As used herein the term "metal or semi-metal coordinating complex" refers to a metal or a semi-metal that coordinates to the nitrogen atoms within the phthalocyanine core moiety. Within these embodiments, in some instances, M is a trivalent or tetravalent metal or semi-metal coordinating complex. Still in other embodiments, M comprises a transition metal or a semi-metal. The term "semi-metal" refers to a chemical element that has properties in between those of metals and nonmetals. Specifically, the term "semi-metal" refers to boron, silicon, germanium, arsenic, antimony, tellurium, aluminum, selenium, polonium and astatine.

In one particular embodiment, M comprises an element selected from the group consisting of vanadium, indium, gallium, aluminum, titanium, tin, lead, bismuth, manganese, and phosphorus.

It should be appreciated that the metal or the semi-metal can be an oxide, a halide, or a combination thereof. For example, and without any limitation, M can be titanium oxide (TiO), indium chloride (InCl), vanadium oxide (VO), gallium chloride (GaCl), and aluminum chloride (AlCl), etc.

In one particular embodiment of the invention, $R^{W1}$ and $R^{W2}$ form a conjugated side-strapped substituent. Within this embodiment, in some instances, $R^{E1}$ and $R^{E2}$ form a conjugated side-strapped substituent. Still in some cases, such a compound has 2-fold symmetry, i.e., the conjugated side-strapped substituents of $R^{W1}$ and $R^{W2}$ are identical to the conjugated side-strapped substituents of $R^{E1}$ and $R^{E2}$.

Other aspects of the invention provide an electronic device comprising a compound disclosed herein. Such electronic devices comprise an optoelectronic device, a photovoltaic, a semi-conductor, a solar cell, a field-effect transistor, organic light emitting diode, or a combination thereof.

Some of the advantages of the conjugated side-strapped phthalocyanine compounds of the invention include, but are not limited to, providing for the production of inexpensive, solution processable chromophores that possess strong absorption in the near-IR region of the solar spectrum (where ca. 40% or available current can be harvested) through self-organized aggregation, accompanied by resultant high charge and exciton mobility necessary for efficient solar electric conversion. The invention also provides a flexible synthetic and characterization strategy that provides a rapid synthesis of derivatives for structure property relationships to be investigated, and characterization in pure thin-film formats, to quantify near-IR photoelectric activities, segregation of dopant dyes (e.g., conjugated side-strapped phthalocyanine compound of the invention) to photoactive interfaces of host donor and acceptor materials in bulk-heterojunction films. Some of the discoveries by the present inventors that are disclosed herein include methods for producing novel near-IR absorbing conjugated side-strapped phthalocyanine compounds and thin film materials, and new OPV platforms using the same.

It has been shown that near-IR dopants enhance spectral response. For example, it has recently been demonstrated that "ternary planar heterojunctions" can be formed with small molecules where a guest, near-IR absorbing compound (e.g., TiOPc) sits between a donor and acceptor phase. Near-IR spectral response was added to the OPV because of the aggregation of that dye, which is not possible with many small molecule guest dyes. The interfaces formed between the donor/guest dye (i.e., molecule or compound) and acceptor/guest dye help to determine both $V_{OC}$ and $J_{SC}$, and interface dipole effects at these interfaces (changing local vacuum levels) are believed to be critical in attempts to dope organic dyes into BHJ OPV device platforms. Solvent annealing of as-deposited TiOPc and ClInPc films, before or after deposition of an electron acceptor ($C_{60}$,) textures the resultant heterojunction, has been shown to enhance photocurrent, and extends photoactivity out to 900 nm, due to the formation of the "Phase II" aggregates of these Pcs.

It has also been shown that soluble TiOPc derivatives can be solution processed into near-IR active thin films. Previously, the present inventors have reported the preparation of soluble TiOPc derivatives, see *J. Org. Chem.*, 2010, 75, 7893-7896, which is incorporated herein by reference in its entirety, and have recently extended this series to other tri- and tetravalent metal Pc/Ncs (e.g. VOPc, ClINc, ClGaPc, ClAlPc and naphthalocyanine ("Nc") analogues) that have a similar molecular shape and potentially a similar morphology in the condensed phase. See, also, commonly assigned U.S. patent application Ser. No. 13/635,324, which is also incorporated herein by reference in its entirety. The present inventors have discovered that the solution-processed thin-films of the soluble octakis(alkylthio)TiOPc derivatives maintained the near-IR-absorbing morphologies of vapor deposited thin-films of TiOPc. Interestingly, the side chains needed to impart solution processability do not appear to significantly impede the aggregation of TiOPc monomers, which leads to a charge transfer band in the near-IR, arising from strong interactions between opposing oxo-titanium groups in adjacent Pcs, as seen in the crystalline forms of TiOPc, suggesting that these dipolar interactions are strong enough to override some of the side chain interactions which might have frustrated that aggregation. The optical properties of these films are reminiscent of Phase-I and -II polymorphs of crystalline TiOPc, verified by XRD studies on powder and thin-films that indicated the presence of a mixture of $COl_{hex}$ and triclinic unit cells.

Soluble TiOPc derivatives are active for solar electric conversion in the near-IR. Soluble TiOPc derivatives have been incorporated into both PHJ and BHJ OPVs with $C_{60}$ and PCBM as the acceptor materials, respectively. Thus, a similar method can be used to produce OPVs using compounds of the present invention. It should be noted that PHJ OPVs using a compound of the invention and $C_{60}$ electron acceptor layers showed good dark (diode) rectification, and reasonable $V_{OC}$ and $J_{SC}$ for the un-optimized OPVs. Successfully fabricated BHJ solar cells used soluble TiOPc a compound of the invention and PCBM as the acceptor. The deposition conditions were optimized at a 1:3 a compound of the invention/PCBM ratio that AFM confirmed led to a pattern of phase segregation characteristic of BHJ active layers. For un-optimized BHJ devices with a ITO/PEDOT:PSS/a compound of the invention:PCBM/LiF/Al architecture, the $V_{OC}$ is (a) higher than the corresponding solution-processed PHJ device fabricated from a compound of the invention and (b) comparable to the vacuum-deposited PHJ fabricated from Phase-I of crystalline TiOPc. Although these cells showed only modest power conversion efficiencies, likely due to poor mobility of the active materials, they exhibited disproportionate solar electric conversion in the near-IR region as revealed by the absorbed photon to current efficiency (APCE) data. The near-IR absorbance band from the Phase II polymorph is low intensity in the absorbance spectrum, yet both the IPCE and the APCE spectrum revealed a significant contribution from this band at ca. 870 nm, indicating that this material is capable of significant solar electric energy conversion further into the near-IR than any known OPV active material to date.

The compounds of the invention can be used in solar cells and OPVs and other electronic devices as discussed herein. Any of the methods known to one skilled in the art, including those disclosed above, can be used to produce various electronic devices comprising a compound of the invention.

As disclosed herein, compounds of the invention are synthetically readily accessible and exhibit many of the desired and/or improved properties compared to conventional phthalocyanine compounds. Compound 1 in FIG. 1 shows one particular example of a rigid "side-strapped" trans-$A_2B_2$ phthalocyanine compound. Spectroscopic characterization of this compound revealed a typical Q-band solution spectrum with a bathochromic shift in the drop-cast thin film (FIG. 3A). AFM imaging of a drop cast film of 1 on HOPG (FIG. 2) reveal microcrystalline layered structures with layer plane thicknesses of ca. 2.5 nm consistent with the "tape-like" orientations and close to the expected long-axis dimensions of this phthalocyanine compound. X-ray thin film diffraction data FIG. 3B suggest comparable c-axis dimensions to the layer-plane dimensions observed in the AFM images. Some of the possible variations of Compound 1 to modify the energetics, solubility, crystallinity, and solid state arrangement include (i) component A, where variation in attachment atoms ($CH_2$, O, or S) can be used to modify energetics as well as packing geometry; (ii) component B where the benzene ring can be replaced with related structures including, but not limited to, moieties such as imide, phthalimide, thiadiazole, thiophene, etc. to modify energetics (IP, EA) while maintaining conjugation; (iii) component C, where the variation in valency of metal center (e.g., di-, tri- or tetravalent metal) affects chromophore stacking in condensed phase; (iv) component D, where unsubstituted regions ensure close packing of chromophores similar to crystalline TiOPc thereby providing coherent aggregation for high charge mobility; (v) component E, where extended conjugation and non-peripheral substitution on Pc core modifies bandgap; and (vi) component F, where the length and nature of side-chains can be used to modify or modulate solubility, crystallinity, crystalline morphology, and blending property with other active material phases.

As disclosed herein, a modular synthetic strategy can be used to produce compounds of the invention including those having 2-fold symmetry. Compounds of the invention are (a) solution processable, (b) near-IR absorbing in aggregated condensed phase polymorphs similar to TiOPc, (c) capable of acting as the primary donor in Type I two-component OPVs (Class I dyes), and/or (d) equipped with electron acceptors and electron donors moieties, providing for selective solubility at donor polymer/electron acceptor interfaces in Type II ternary OPVs (Class II dyes). In Type I platforms, aggregates are designed to provide good near-IR photoactivity and coherence in the aggregate ("tape-like" structures) leading to high charge (hole) mobilities. For Type II platforms, materials are designed to localize at the D/A interface, through self-assembly, and in their optimized forms, to act as "guest" dye compatibilizers for the donor and acceptor phases of the BHJ active layer. Phase separation motifs were characterized using combinations of transmission and reflectance UV-visible spectroscopies, X-ray diffraction, low angle X-ray scattering, and vibrational spectroscopies (IR, Raman). As used herein, the term "near-IR absorbing" refers to ability to absorb light having wavelength of about 700 nm or longer, typically about 800 nm or longer, and often about 1000 nm or longer, and extending to about 2500 nm (2.5 microns). Alternatively, compounds of the invention typically absorb wavelength of from about 200 nm to about 1000 nm, often from about 200 nm to about 800 nm, and more often from about 200 nm to about 750 nm.

In some aspects of the invention, the compounds of the invention are used as dopants to produce p-type semiconductors or photovoltaics. P-type semiconductors have a larger hole concentration compared to electron concentration. It is believed that these holes are the majority carriers and electrons are the minority carriers. Thus, in some instances the compositions of the invention include intrinsic p-type or n-type semiconductors doped with a compound of the invention. It should be appreciated, however, in some instances, compounds of the invention can also be used to produce n-type semiconductors or photovoltaics.

Yet in other aspects of the invention provides solar cells comprising a compound of the invention as dopants.

Figure 7:
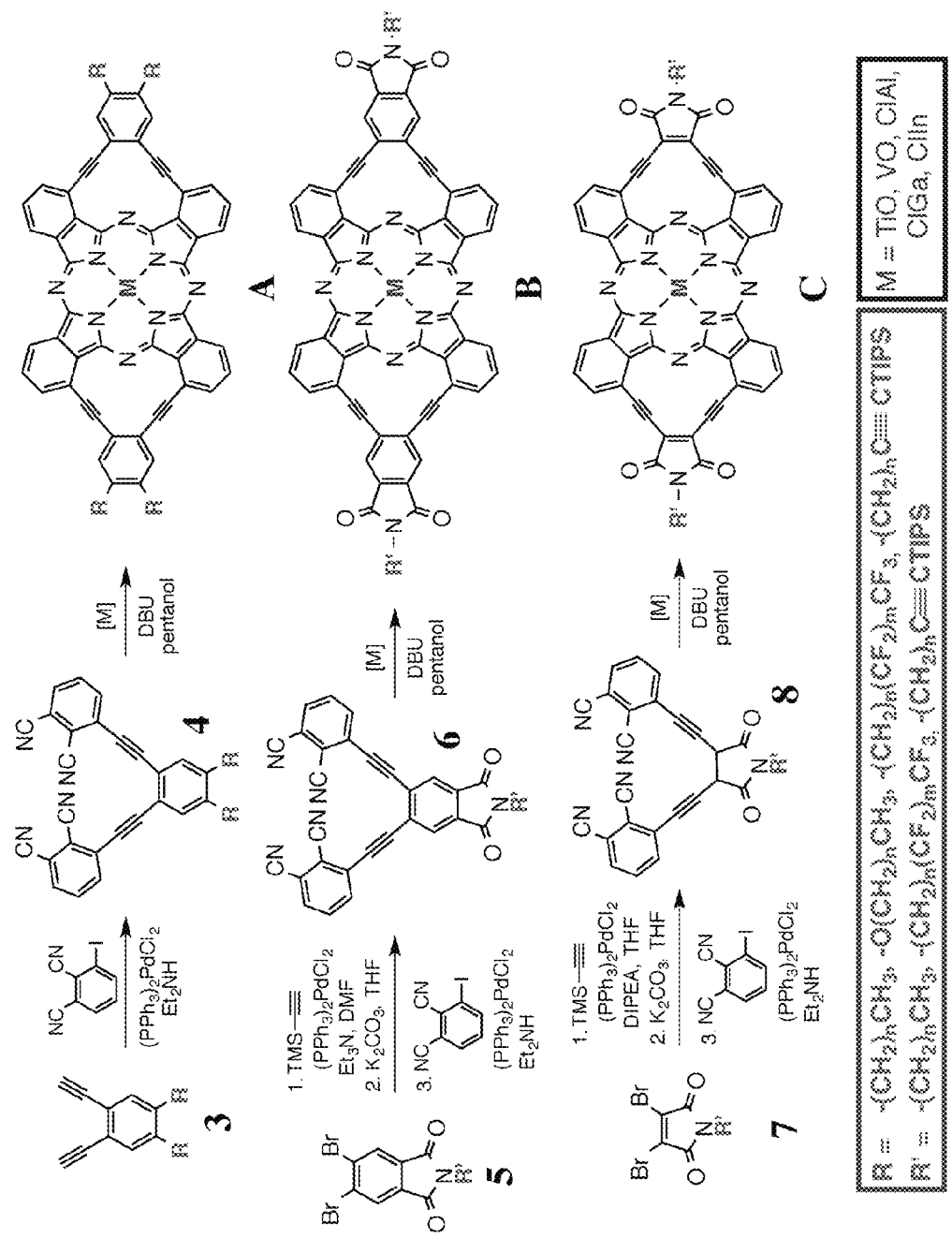
FIG. 7 shows one of the reaction schemes used to produce some of the compounds of the invention. Class I dyes (and precursors to Class II dyes) are produced by synthesis of trans-$A_2B_2$ Pc/Nc scaffolds. Compounds A, B and C shows some of the different aromatic ring systems and substituents.
Figure 8:
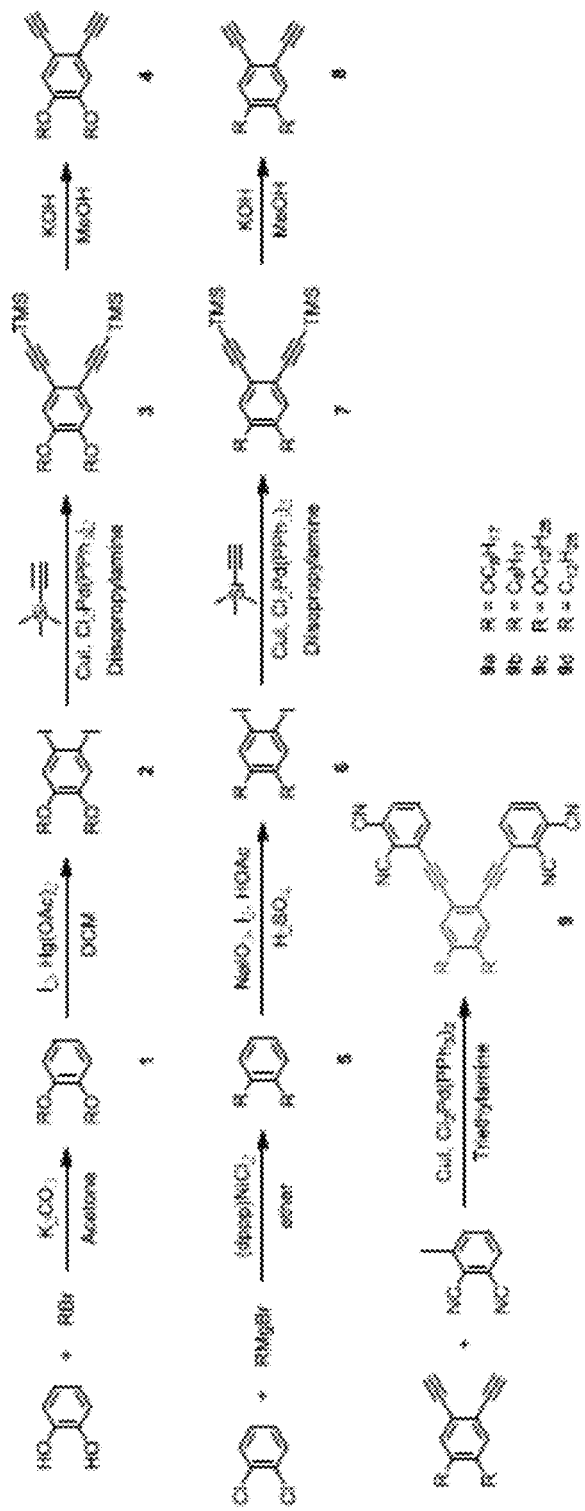
FIG. 8 shows another reaction scheme that was used to produce various starting materials in preparation of compounds of the invention.

Compounds of the invention can be synthesized using inter alia a general procedure disclosed in, for example, FIG. 7 and FIG. 8. As can be seen, by changing the starting material one can synthesize a wide variety of compounds. Using similar procedures shown in FIG. 7 and FIG. 8, a wide range of compounds of the invention can be prepared.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

Examples

Synthesis of Compounds of the Invention for Self-Aggregation and Isolation at Organic-Organic Interfaces Three scaffolds of 2-fold symmetry compounds of the invention are illustrated for Class I and Class II dyes (FIG. 7), each having "side-strapping" moieties, a term used to describe substituents that induce selective formation of the trans-$A_2B_2$ chromophore architecture. In FIG. 7, this "side-strapping," in concert with the apical ligand of the tri/tetravalent metal center, is believed to induce a one-dimensional ordering of the chromophores in the condensed phase that is believed to influence aggregation and segregation in both Type I and Type II OPV platforms. A related approach to 2-fold symmetric Pc chromophores was recently shown to successfully increase Pc-Pc interactions relative to symmetrically substituted dyes, resulting in markedly increased field-effect hole mobilities as a consequence. Some Class I dyes have alkyl, fluoroalkyl, alkoxy, and thioalkyl peripheral groups (R/R'), while some Class II dyes have donor and/or acceptor moieties by utilizing the acetylenic peripheral groups for click chemistry.

Class I Dyes Produced by Side-Strapped Phthalocyanine Synthesis:

Scaffolds A-C were prepared from rigid bisphthalonitriles 4, 6, and 8 (see FIG. 7), with the increased conjugation expected to enhance aggregation and lower the bandgap (increasing near-IR absorption). A wide range of transport HOMO energies are available through modulation of the R groups in A in combination with the imide bridges in B and C (vide infra, FIG. 4). Bisphthalonitriles 4, 6 and 8 provided the trans-$A_2B_2$ Pc architectures selectively. Rigid bisphthalonitriles 4 can be prepared by Pd-catalyzed coupling of o-diethynyl benzene 3 with 3-iodophthalonitrile. Imide-containing bisphthalonitriles 6 and 8 can be prepared from 3,4-dibromophthalimide 5 and 3,4-dibromomaleimide 7, respectively, by Pd-catalyzed cross-coupling with trimethylsilylacetylene, followed by deprotection, and then a second Pd-catalyzed cross-coupling with 3-iodophthalonitrile. All bisphthalonitrile precursors can be prepared with several different peripheral R/R' groups, including acetylene moieties for click chemistry. Naphthyl analogs can be prepared using the corresponding iodo- and nitronaphthalonitriles (not shown) which is obtainable from the hydroxyl compound (i.e., 1-hydroxynaphthalene, 2,3-dicarbonitrile).

The modular nature of the synthesis allows multiple variations of the core structure (FIG. 1). In such a manner, a library of compounds of the invention were and can be produced that include variation at the metal center M, e.g., by using metal sources $Ti(OR)_4$, $V(acac)_2$, $AlCl_3$, $GaCl_3$, and $InCl_3$ to produce a library of compounds comprising TiO, VO, ClAl, ClGa, and ClIn derivatives of compounds of the invention. In addition, a library of compounds of the invention comprising both phenyl or naphthyl ring system compounds can be produced. Moreover, compounds whose substituent side chains R/R' including alkyl, alkoxy, and perfluoroalkyl, as well as acetylenic moieties for click chemistry (vide infra) can also be produced.

Class II Dyes Produced by Click Chemistry Modification of Class I Dyes.

Figure 4:
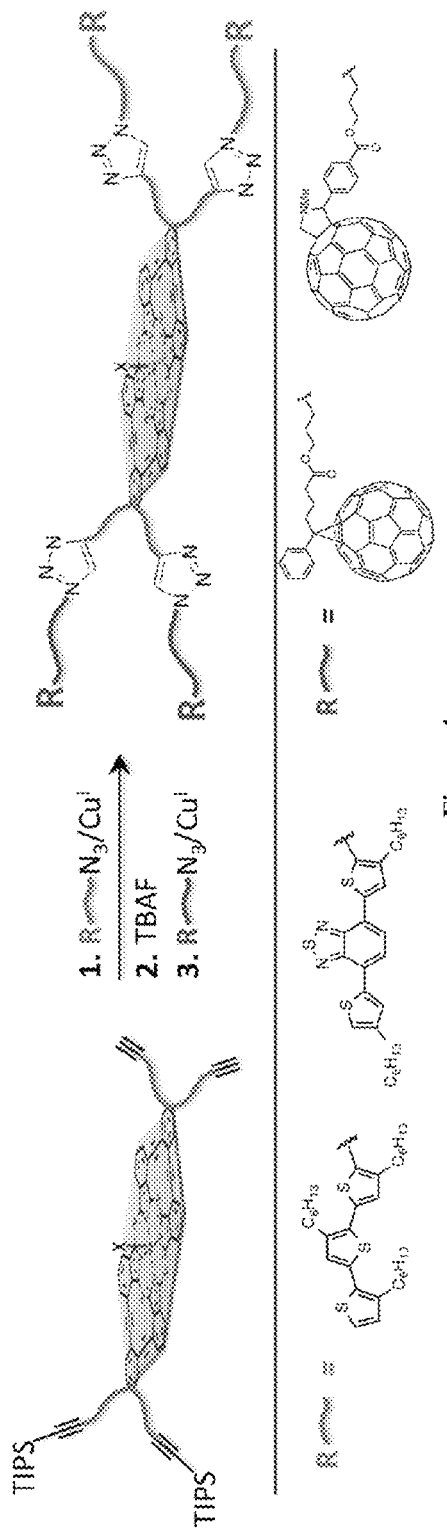
FIG. 4 shows one possible method of producing compounds of the invention. In particular, "click chemistry" approach to Class II dyes, azides are coupled to acetylenic residues on scaffolds A-C of FIG. 7 (scaffold A shown) under CuAAC conditions to provide periphery moieties on the Pc/Nc. Illustrated in this Figure are the thiophene, benzothiadiazole, and fullerene moieties and analogs as active layer compatiblizers.

Mixed "Donor-Pc-Acceptor" Class II dyes are designed to act as compatibilizers of the donor and acceptor active materials and isolate at the D/A interface. Oligothiophene and thiophenyl benzo-thiodiazole (i.e. TBT) groups were used to determine compatibility with P3HT and PCDTBT donor polymers, respectively, and fullerene derivatives for compatibility with PCBM acceptor phases. These are example structures that were used as a starting point—as reduction of interfacial energy in active layers depends strongly on molecular architecture. Click chemistry approach to these materials is illustrated in FIG. 4. The copper(I)-catalyzed azide-alkyne cycloaddition (CuAAC) reaction was characterized by extraordinary reliability and functional group tolerance. This process has proven useful for the synthesis of novel materials, and has been demonstrated as a suitable reaction for Pc/Nc modification due to its extremely high yields and fidelity. Chromophores with peripheral acetylenic linkages from scaffolds A-C provided access to many new materials with different substituents on the side-strapped moieties via the corresponding azides. Selective silyl protecting group chemistry for the acetylenic moieties was employed to prepare the mixed "Donor-Pc-Acceptor" Class II dyes shown and related derivatives.

Library Design Variables:

The particular variables in this library of Class I and Class II dyes were chosen to address (i) the ability of other nonplanar tri- and tetravalent MPcs besides TiOPc to exhibit extensively red-shifted thin-film Q-band spectra (variable metal centers M); (ii) the additional conjugation in scaffolds A and B, also present on the Nc chromophore relative to Pc chromophore, that results in a bathochromic shift in solution of ca. 50-100 nm and potentially much greater than that in the condensed phase; and (iii) the effect provided by different substituents on the condensed phase morphologies of these chromophores (variable R/R' groups). Additionally, all three chromophore scaffolds, A-C, are substituted in the non-peripheral positions of the Pc/Nc core, which is known to significantly decrease the bandgap of Pc/Nc chromophores relative to peripheral substitution, although the effect on morphology of tetravalent MPc analogs is unknown. A non-peripherally substituted TiOPc derivatives were prepared that exhibited both a large bathochromic Q-band shift (850 nm in sol'n; 960 nm in thin-film) as well as crystallographic evidence of chromophore-chromophore interaction in the solid state. DFT calculations (B3YLP/6-31G*) suggested bandgap and FMO energies (FIG. 5) for chromophores A were consistent with other TiOPcs (e.g., HOMO ca. 5.1 eV), with modulation provided by the side-chain substitution. The imide moieties in B and C modulated the predicted FMO energies to higher IP (HOMO ca. 5.7 and 5.9 eV, respectively), which for Type I OPVs lead to a substantially higher $V_{OC}$ than seen for the crystalline materials, and for Type II platforms, and allowed these guest dyes to be used in conjunction with high IP host polymers (e.g., PCDTBT), while introducing good near-IR response and retention of high $V_{OC}$ in the OPV platform.

Thin-Film Fabrication and Optical Characterization:

Thin-films were fabricated from all new materials on quartz substrates using spin-coating or casting (doctor-blading) techniques with variations in concentration, spin rate, solvent, and substrate pre-treatment. Visible-near-IR transmission and reflectance spectroscopies were used to characterize Q-band shape and position as a qualitative indicator of aggregation type, and the extent of conversion of these Pcs to Phase II-like polymorphs. Of particular interest are the orientations of these new Pc aggregates at 1-2 monolayer coverages, since these orientations help to determine photoelectrical activity and solution rates of electron transfer that are related to OPV performance. Ordered side-chain-modified Pc thin films can be deposited using Langmuir-Blodgett film compression and horizontal transfer which then provides known thickness films with reasonable long range order. 1-2 monolayer films of compounds of the invention can be formed on device-relevant hole-collection electrodes, and characterized the average orientation of these films, arising from measurements of absorbance dichroism ($A_{TE}/A_{TM}$), as a function of deposition and post-deposition processing conditions (including thermal and solvent annealing treatments), and in the presence of fullerene acceptors in these thin films.

Polymorph Characterization by X-Ray Diffraction and Reflectivity:

The nanometer and micron scale organization of these new near-IR absorbing thin-films are investigated using combinations of X-ray powder and thin film diffraction (XRD) to determine the coherence and the type of packing within these thin-film assemblies, especially as a function of temperature. These experiments are conducted first with single-component Pc or Nc films, and later using mixtures of the donor Pc or Nc with a fullerene acceptor, with varying D/A ratios, to characterize the extent to which aggregate ordering are retained when D/A mixtures are formed. Adequate mixing of these phases is made so that crystalline domain sizes are reduced below the X-ray diffraction coherence limit, and diffraction patterns suggest nearly amorphous films. For adequately coherent films, it is found that X-ray reflectivity (XRR) studies are useful in suggesting orientation and packing geometries in Pc thin films whose optical and structural properties are more readily interrogated using both XRD and XRR. AFM studies are used to determine the degree of coherence in these thin-films and infer local ordering. As shown in the AFM image of FIG. 2, side-strapped TiOPcs deposited on HOPG and clean Au substrates formed microcrystallites with the requisite layered structures, consistent with the "tape-like" orientations suggested in FIG. 2, with layer plane separations close to the expected long-axis dimensions of these Pcs. X-ray thin film diffraction data showed monoclinic unit cells, two molecules per cell, with comparable c-axis dimensions to those suggested in the AFM data.

Characterization of Frontier Orbital Energies for Pc and Nc Aggregate Films, Single-Component and D/A Blended Heterojunctions:

Using established photoemission spectroscopic protocols, using both He(I) and He(II) excitation, the ionization potential (IP) and HOMO energies of these new assemblies are characterized on both device-relevant substrates (e.g., ITO and ITO/interlayer contacts) and on highly-ordered-pyrolitic-graphite (HOPG), where more ordered Pc or Nc films are expected. UPS capabilities are used to determine the differences in HOMO and IP for these new assembles, relative to their crystalline counterparts, as a function of surface coverage, degree and type of aggregation, and when planar heterojunctions are formed with vacuum deposited $C_{60}$ over the Pc/Nc film, or when BHJ films are formed with soluble acceptors such as PCBM. UPS system permits spectral acquisition at very high sensitivity, with a dynamic range in cts/sec of at least $10^3$, full removal of satellite peaks, allowing one to characterize the energetic dispersity of the Pc or Nc HOMO peak, and to characterize "band-tailing" and mid-gap state formation as a function of the degree of aggregation and coherence, which can greatly affect the population of states that cause charge trapping and recombination in OPV platforms. Studies to determine the extent to which this band tailing is mitigated, or made worse in vacuum deposited BHJ Pc/$C_{60}$ platforms, is extrapolated as well to mixed Pc- or Nc/fullerene films.

In addition, the differences in offsets in frontier orbital energies of these new Pc or Nc dyes are characterized as a function of coverage of a crystalline acceptor such as $C_{60}$ (PHJ platforms), or as a function of concentration of a soluble acceptor such as PCBM, where previous experiments have clearly shown that there can be significant interface dipoles formed at the D/A interface, resulting in significant shifts in local vacuum levels, and changes in the transport HOMO and LUMO levels of both D/A components, which ultimately control the probability of photocurrent formation, and open-circuit photovoltage. He(I) UPS is used as a means of estimation of the transport HOMO levels from both the target Pc/Nc systems, and these molecules as ultra-thin films in contact with a polymer host such as P3HT. It is desired to be able to ascertain whether the transport HOMO levels of the Pc/Nc aggregates are well matched to the same levels in the host donor polymer, since if they are not, there may be a substantial risk that a Pc/Nc aggregate located at a donor/acceptor interface will simply act as a charge trap and recombination center. The transport HOMO levels for crystalline TiOPc and ClInPc are well matched to those estimated for the donor polymer PCDTBT but higher than those reported for P3HT.

From a thermodynamic perspective alone it is expected that hole transfer to a high IP host like PCDTBT will be facile. For surface confined Pcs, lower IPs than seen for the crystalline dyes are observed, and for such dyes P3HT may be a useful host polymer. The IP estimated for some of the compounds of the invention are high (>5.1 eV) and suggest that all of the high IP host polymers may provide thermodynamically for efficient hole capture. The high IP in the compounds of the invention opens up possibilities for $V_{OC}$ approaching 1 volt in OPV platforms where charge extracting contacts have been properly optimized and no long limit the output power of the device platform.

Investigating Electrical and Optical Properties as they Pertain to OPV Performance:

The optical and electrical properties of highest rated films comprising a compound of the invention was examined as isolated thin films on conductive substrates, and incorporated into either planar or bulk-heterojunction device formats.

Figure 6:
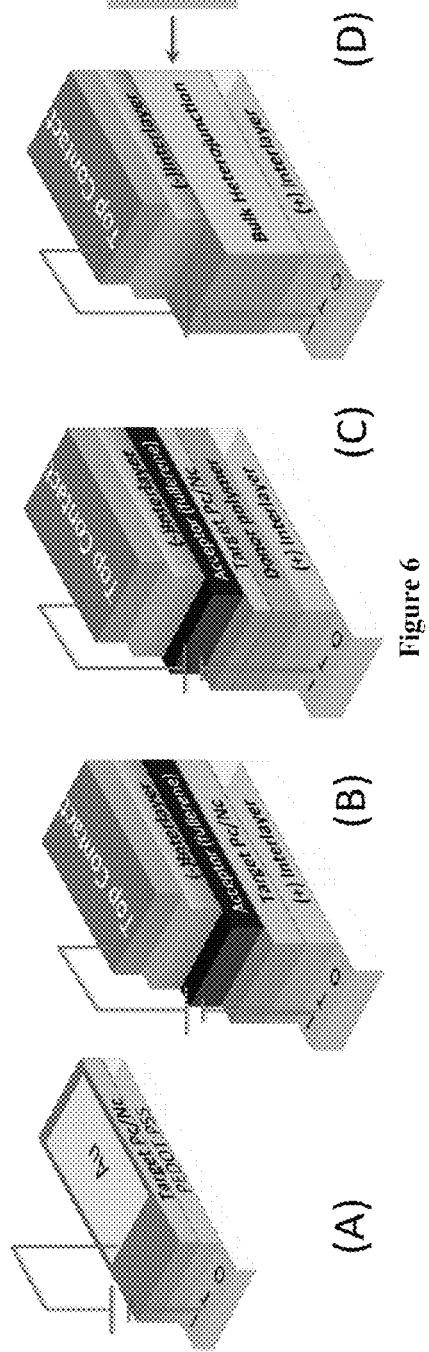
FIG. 6 shows various device configurations to characterize the electrical properties of assemblies comprising a compound of the invention. Panel (A) shows a hole-only device consisting of high work function top (Au) and bottom (e.g. PEDOT:PSS on ITO) contacts. Panel (B) shows type I platforms involving either a PHJ configuration (shown here) or a BHJ configuration, where a compound of the invention is used as the sole donor layer. The PHJ configuration is used first, to ascertain degree of aggregation of a compound of the invention and its effect on rectification and OPV performance, moving later to BHJ configurations where optimization of dispersion of the donor/acceptor phases is achieved. These thin films are sandwiched between a hole-selective interlayer, and a solution or vacuum deposited acceptor layer. Panel (C) shows a planar heterojunction configuration where an ultra-thin film of a compound of the invention is sandwiched between solution processed donor and acceptor layers—in this configuration thermal or solvent annealing initiates migration of the Pc/Nc layer into either the donor or acceptor layer, in a fashion that allows monitoring optically and electronically. Panel (D) shows the bulk heterojunction configuration where a compound of the invention donor is combined with donor polymer and acceptor.

Estimation of Hole Mobilities as a Function of Pc or Nc Structure and Processing Conditions:

"Hole-only" device platforms (FIG. 6) are created where the Class I or Class II Pc/Nc film was sandwiched between high work function contacts (e.g., ITO/PEDOT:PSS/Pc or Nc/MoOx/Ag) where current/voltage (J/V) curves are recorded as these devices are driven from ohmic into space-charge limited regimes (SCLC) providing estimates of hole-mobilities relative to established materials (e.g. P3HT films, vacuum deposited CuPc). These studies are especially desirable for Type I OPV platforms. Where the Pc/Nc is the primary donor, both exciton dissociation and hole-transport in the Pc/Nc film are important to device performance, and need to be balanced with electron transport mobilities in the acceptor phase. Molecular structure, processing solvent, and temperature strongly influence molecular overlap, which impacts on charge mobilities in what is believed to be "tape-like" structures in coherent materials of the present invention. Using conducting (Pt) tip AFM of thin films of the Pc shown in FIG. 2, the J/V properties were mapped out at multiple positions on these thin films. In regions demonstrating good electrical contact with the substrate electrode (ITO or Au), it was determined from the SCLC J/V responses that hole-mobilities were at least $10^{-2}$ cm$^2 \cdot$volt$^{-1} \cdot$sec$^{-1}$ which is higher than for most conventional (crystalline) Pc thin films, and approaching some of the top performing polymer donors in the best efficiency OPVs.

Electrical Properties of Prototype OPV Platforms:

In addition to hole-only devices, the electrical properties of platforms comprising a compound of the invention that are designed to provide both optical and electrical characterization (FIG. 6) are evaluated. OPV platforms include: (i) Type I PHJ configurations (shown in FIG. 6, Panel B) or a BHJ configuration, where a compound of the invention was used as the sole donor layer. These platforms provide a convenient means to optically characterize the thin film during processing steps, and to optimize aggregation of a compound of the invention as a neat film, and in combination with the small molecule acceptor. The PHJ configuration is used to ascertain degree of aggregation of the compound of the invention and its effect on rectification and OPV performance, moving later to BHJ configurations where optimization of dispersion of the donor/acceptor phases is achieved. Thin Pc films are sandwiched between hole-selective interlayers, and a solution or vacuum-deposited acceptor layer. Compounds of the invention can be used to achieve long range order in these aggregates so as to facilitate both the desired spectral response, and adequate charge mobilities to balance those in the acceptor phase. (ii) A planar heterojunction configuration in which an ultra-thin film of the target Pc/Nc is sandwiched between solution processed donor and acceptor layers (using orthogonal solvents and/or vacuum deposition to deposit planar heterojunction configurations)—in this configuration thermal or solvent annealing initiated controlled movement of the compound of the invention layer into either the donor or acceptor layer, in a fashion that can be monitored optically and electronically. Changes in dark rectification, series resistance, $J_{SC}$ and $V_{OC}$ and IPCE/APCE are monitored as a function of penetration of the compound of the invention into either the donor polymer or acceptor phases. For these experiments, the use of the chloro-indium version of a compound of the invention is used, X-ray fluorescence probabilities permit XRF mapping (at ca. 25 nm length scales, on smooth substrates) using field-emission SEM. And (iii) bulk heterojunction configurations where the compound of the invention donor is combined with donor polymer and acceptor in concentration ratios guided by planar heterojunction experiments.

Device platforms are configured to allow for transmission absorbance measurements at any stage of device formation, allowing characterization of the degree and type of aggregation of the compound of the invention. In addition, hole- and electron-selective interlayers, or interlayers which enhance hole- or electron-collection, is used to remove contact issues as limiters of J/V properties and OPV performance.

Recent studies of multilayer small molecule and polymer platforms created by deposition from orthogonal solvents suggest a convenient means to approach the problem of identifying in which layer a compound of the invention will prefer to reside, or whether sharp interfaces can be formed between each material which withstand annealing via solvent exposure and/or thermal stress. The Q-band spectral response of these systems is a sensitive indicator of aggregation (or presence of monomeric species), and previous studies suggest that the migration of aggregates comprising a compound of the invention into either the donor or acceptor phases can be monitored, either as neat films, or in OPV device platforms complete with contacting electrodes.

Photocurrent Spectroscopies Of Prototype OPV Platforms:

This experiment focused on photocurrent efficiency spectra (incident photon current efficiency—IPCE and absorbed light current efficiency—APCE) in both Type I and II platforms. Structure of the compound of the invention was correlated to degree of aggregation in condensed phases (absorbance data), and efficiency of photocurrent production (IPCE and APCE spectra). Characterization of OPV platforms under simulated AM1.5 illumination conditions often fails to provide mechanistic information available from IPCE and APCE characterization, and it is desirable to quantify the percentage of photocurrent created from each aggregate type (Type I platforms), or the percentage of photocurrent created relative to the host polymer (Type II platforms). IPCE spectra shows how incident light efficiencies were dictated by polymorphic structure. APCE spectra provides more mechanistic detail—these spectra show the relative exciton dissociation efficiencies of absorbed light partitioned between different polymorphs, and often show that the highest photocurrent production probabilities belong to the near-IR absorbing polymorphs. IPCE and APCE spectra are collected at far reverse bias, where photo-generated charge carriers are harvested with insignificant recombination losses, and near the maximum power point, where photo-current generation competes with both bulk and surface recombination. Electron acceptors and contact/interlayer materials are used that maximize $V_{OC}$, and interlayers on the hole-collection side which are high work function, and which facilitate efficient hole extraction. This experiment allows understanding of the science underpinning limitations to energy conversion efficiency, and $V_{OC}$ specifically, arising from hole- and electron-extracting contact materials.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All references cited herein are incorporated by reference in their entirety.

What is claimed is:

1. A conjugated side-strapped phthalocyanine compound of the formula:

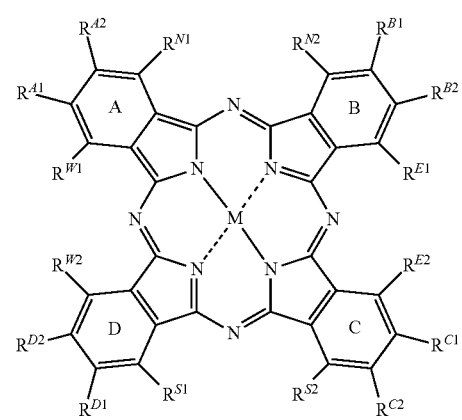

wherein

M is a phthalocyanine coordinating moiety;

at least one pair of $R^{W1}$ and $R^{W2}$, or $R^{N1}$ and $R^{N2}$, or $R^{E1}$ and $R^{E2}$, or $R^{S1}$ and $R^{S2}$ form a conjugated side-strapped substituent and the remaining are independently selected from the group consisting of:

(i) H;

(ii) $C_1$-$C_{25}$ alkyl;

(iii) a moiety of the formula: $-(CH_2CH_2O)_a-(CH_2)_bOR_{a1}$, $-(CH_2CH_2O)_a-(CH_2)_bNR_{a2}R_{a3}$, $-(CH_2CH_2O)_a-(CH_2)_bCONR_{a2}R_{a3}$, $-(CH_2CH_2O)_a-(CH_2)_bCN$, $-(CH_2CH_2O)_a-(CH_2)_bCl$, $-(CH_2CH_2O)_a-(CH_2)_bBr$, $-(CH_2CH_2O)_a-(CH_2)_bI$, $-(CH_2CH_2O)_a-(CH_2)_b$-Phenyl, or $-(CH_2CH_2O)_a-(CH_2)_b$-ethynyl;

(iv) an aryl or a heteroaryl group of the formula

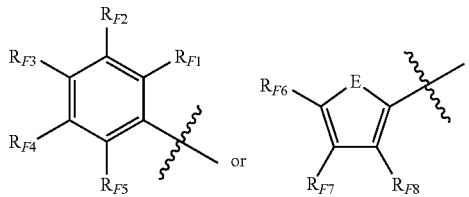

wherein E is S, O, or NH, and $R_{F1}$, $R_{F2}$, $R_{F3}$, $R_{F4}$, $R_{F5}$, $R_{F6}$, $R_{F7}$, and $R_{F8}$ are independently selected from the group consisting of:
(a) H;
(b) $C_1$-$C_{25}$ alkyl;
(c) a moiety of the formula: —$(CH_2CH_2O)_a$—$(CH_2)_bOR_{a1}$, —$(CH_2CH_2O)_a$—$(CH_2)_bNR_{a2}R_{a3}$, —$(CH_2CH_2O)_a$—$(CH_2)_bCONR_{a2}R_{a3}$, —$(CH_2CH_2O)_a$—$(CH_2)_bCN$, —$(CH_2CH_2O)_a$—$(CH_2)_bCl$, —$(CH_2CH_2O)_a$—$(CH_2)_bBr$, —$(CH_2CH_2O)_a$—$(CH_2)_bI$, —$(CH_2CH_2O)_a$—$(CH_2)_b$-Phenyl, or —$(CH_2CH_2O)_a$—$(CH_2)_b$-ethynyl;
(d) —$NR_{e1}R_{e2}$, —$OR_{e3}$, and —$SR_{e4}$;
(e) an aryl or heteroaryl group; and
(f) a polymerizable group;
(v) a fused aromatic ring of the formula:

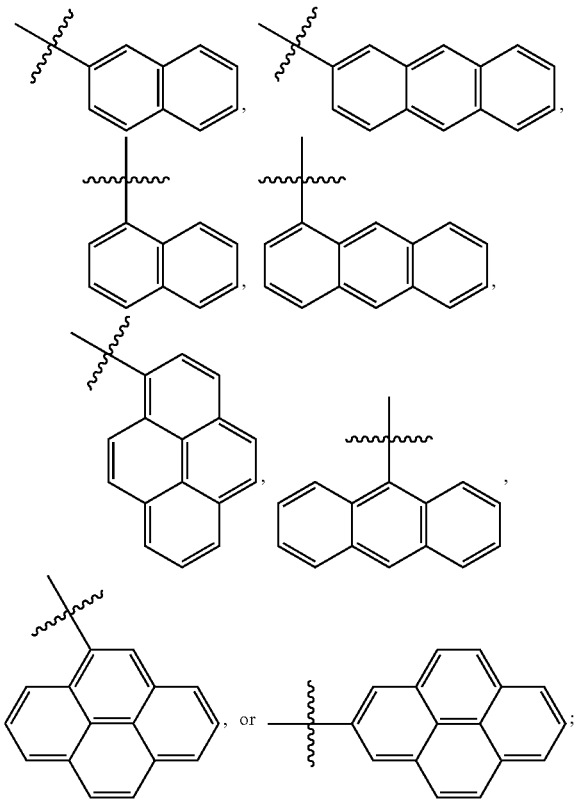

(vi) a polymerizable group selected from the group consisting of vinyl, allyl, 4-styryl, acryloyl, methacroyl, epoxide, acrylonitrile, isocyanate, isothiocyanate, strained ring olefins; —$(CH_2)_dSiCl_3$, —$(CH_2)_dSi(OCH_2CH_3)_3$, and —$(CH_2)_dSi(OCH_3)_3$;

(vii) halide; and
(viii) —$NR_{e1}R_{e2}$, —$OR_{e3}$, or —$SR_{e4}$;
each of $R^{A1}$, $R^{A2}$, $R^{B1}$, $R^{B2}$, $R^{C1}$, $R^{C2}$, $R^{D1}$ and $R^{D2}$ is independently selected from the group consisting of:
(i) H;
(ii) $C_1$-$C_{25}$ alkyl;
(iii) a moiety of the formula: —$(CH_2CH_2O)_a$—$(CH_2)_bOR_{a1}$, —$(CH_2CH_2O)_a$—$(CH_2)_bNR_{a2}R_{a3}$, —$(CH_2CH_2O)_a$—$(CH_2)_bCONR_{a2}R_{a3}$, —$(CH_2CH_2O)_a$—$(CH_2)_bCN$, —$(CH_2CH_2O)_a$—$(CH_2)_bCl$, —$(CH_2CH_2O)_a$—$(CH_2)_bBr$, —$(CH_2CH_2O)_a$—$(CH_2)_bI$, —$(CH_2CH_2O)_a$—$(CH_2)_b$-Phenyl, —$(CH_2CH_2O)_a$—$(CH_2)_b$-ethynyl;
(iv) an aryl or heteroaryl group of the formula

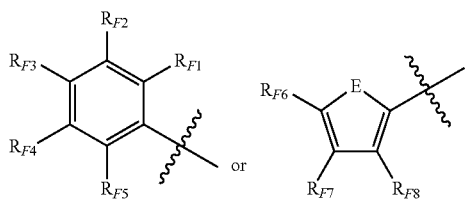

wherein E is S, O, or NH, and $R_{F1}$, $R_{F2}$, $R_{F3}$, $R_{F4}$, $R_{F5}$, $R_{F6}$, $R_{F7}$, and $R_{F8}$ are independently selected from the group consisting of:
(a) H;
(b) $C_1$-$C_{25}$ alkyl;
(c) a moiety of the formula: —$(CH_2CH_2O)_a$—$(CH_2)_bOR_{a1}$, —$(CH_2CH_2O)_a$—$(CH_2)_bNR_{a2}R_{a3}$, —$(CH_2CH_2O)_a$—$(CH_2)_bCONR_{a2}R_{a3}$, —$(CH_2CH_2O)_a$—$(CH_2)_bCN$, —$(CH_2CH_2O)_a$—$(CH_2)_bCl$, —$(CH_2CH_2O)_a$—$(CH_2)_bBr$, —$(CH_2CH_2O)_a$—$(CH_2)_bI$, —$(CH_2CH_2O)_a$—$(CH_2)_b$-Phenyl, or —$(CH_2CH_2O)_a$—$(CH_2)_b$-ethynyl;
(d) —$NR_{e1}R_{e2}$, —$OR_{e3}$, and —$SR_{e4}$;
(e) an aryl or heteroaryl group; and
(f) a polymerizable group;
(v) a fused aromatic ring of the formula:

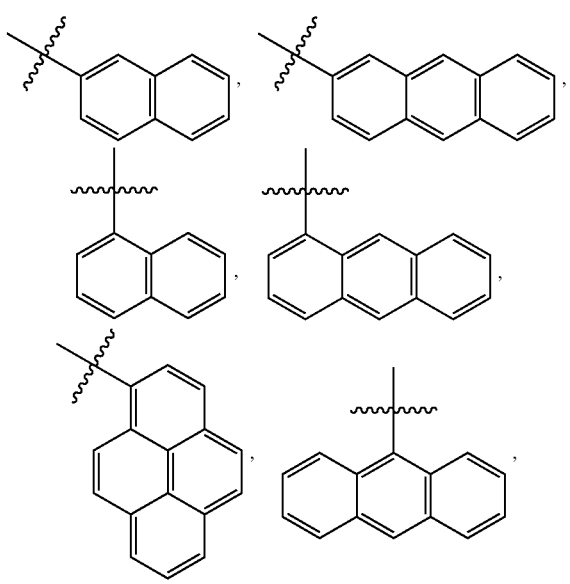

-continued

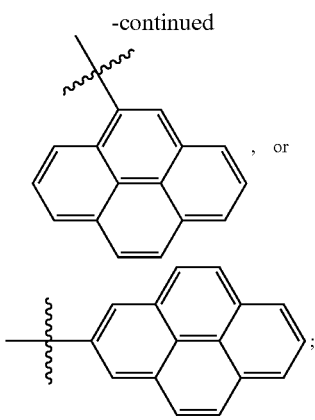, or (vi) a polymerizable group selected from the group consisting of vinyl, allyl, 4-styryl, acryloyl, methacroyl, epoxide, acrylonitrile, isocyanate, isothiocyanate, strained ring olefins; —$(CH_2)_d SiCl_3$, —$(CH_2)_d Si(OCH_2CH_3)_3$, and —$(CH_2)_d Si(OCH_3)_3$;

(vii) halide;

(viii) —$NR_{e1}R_{e2}$, —$OR_{e3}$, or —$SR_{e4}$;

or each pair of $R^{A1}$ and $R^{A2}$, $R^{B1}$ and $R^{B2}$, $R^{C1}$ and $R^{C2}$, and $R^{D1}$ and $R^{D2}$ along with the carbon atom to which they are attached to form an optionally substituted phenyl ring moiety;

a is an integer from 0 to 10;

b is an integer from 1 to 25;

d is an integer between 0 and 25;

each of $R_{e1}$, $R_{e2}$, $R_{e3}$, and $R_{e4}$ is independently selected from the group consisting of:

(a) H;

(b) $C_1$-$C_{25}$ alkyl;

(c) a moiety of the formula: —$(CH_2CH_2O)_a$—$(CH_2)_b OR_{a1}$, —$(CH_2CH_2O)_a$—$(CH_2)_b NR_{a2}R_{a3}$, —$(CH_2CH_2O)_a$—$(CH_2)_b CONR_{a2}R_{a3}$, —$(CH_2CH_2O)_a$—$(CH_2)_b CN$, —$(CH_2CH_2O)_a$—$(CH_2)_b Cl$, —$(CH_2CH_2O)_a$—$(CH_2)_b Br$, —$(CH_2CH_2O)_a$—$(CH_2)_b I$, —$(CH_2CH_2O)_a$—$(CH_2)_b$-Phenyl, or —$(CH_2CH_2O)_a$—$(CH_2)_b$-ethynyl;

(d) an aryl or heteroaryl group; and (e) a polymerizable group; and each of $R_{a1}$, $R_{a2}$, and $R_{a3}$ is independently selected from the group consisting of H, $C_1$-$C_{25}$ alkyl and aryl.

2. The conjugated side-strapped phthalocyanine compound according to claim 1, wherein said conjugated side-strapped substituent is a moiety of the formula:

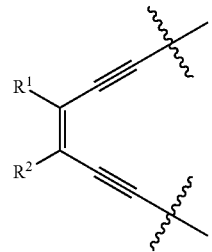

wherein each of $R^1$ and $R^2$ is independently hydrogen, $C_1$-$C_{25}$ alkyl and $C_1$-$C_{25}$ haloalkyl;

or $R^1$ and $R^2$ together with the carbon atom to which they are attached to form aryl, heteroaryl, or heterocyclyl ring structure, each of which is optionally substituted.

3. The conjugated side-strapped phthalocyanine compound according to claim 2 of the formula:

IA

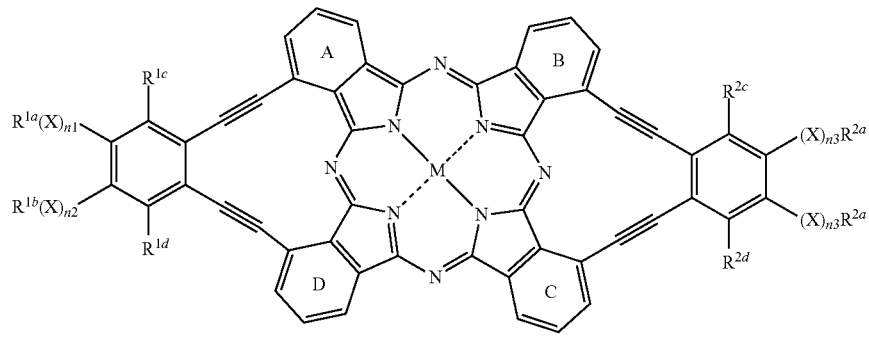

IB

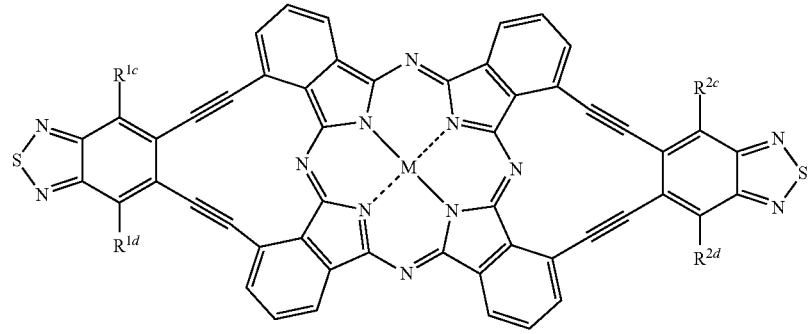

IC

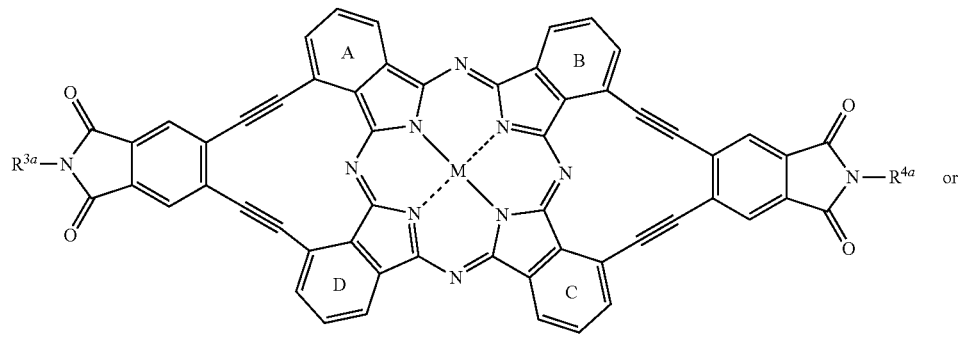

ID

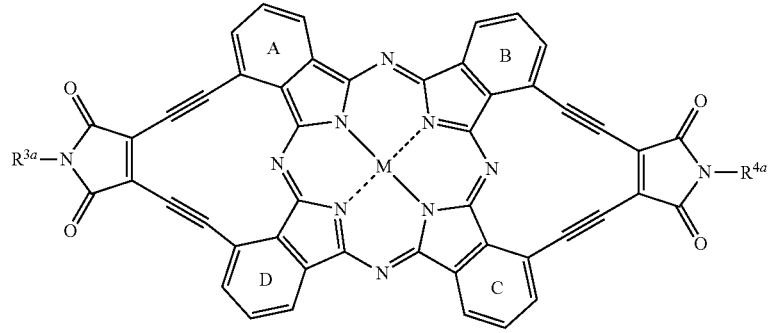

wherein
M, $R^{N1}$, $R^{N2}$, $R^{S1}$, $R^{S2}$, $R^{A1}$, $R^{A2}$, $R^{B1}$, $R^{B2}$, $R^{C1}$, $R^{C2}$, $R^{D1}$ and $R^{D2}$ are those defined in claim 1;
each of $R^{1a}$, $R^{1b}$, $R^{1c}$, $R^{1d}$, $R^{2a}$, $R^{2b}$, $R^{2c}$, $R^{2d}$, $R^{3a}$ and $R^{4a}$ is independently selected from the group consisting of hydrogen, $C_1$-$C_{25}$ alkyl and $C_1$-$C_{25}$ haloalkyl;
each of $n_1$, $n_2$ and $n_3$ is independently 0 or 1; and
X is O or S.

4. The conjugated side-strapped phthalocyanine compound of claim 3, wherein M comprises an element selected from the group consisting of vanadium, indium, gallium, aluminum, titanium, tin, lead, bismuth, manganese, and phosphorus.

5. An electronic device comprising a thin film of a compound of claim 1.

6. The electronic device of claim 5, wherein said electronic device comprises an optoelectronic device, a photovoltaic, a semi-conductor, a solar cell, a field-effect transistor, organic light emitting diode, or a combination thereof.

7. A composition comprising a conjugated side-strapped phthalocyanine compound having 2-fold symmetry and a solubility in tetrahydrofuran (THF) of at least 0.5±0.1 mole/L.

8. The composition according to claim 7, wherein said conjugated side-strapped phthalocyanine compound has a solubility in chloroform of at least 0.5±0.1 mole/L.

9. The composition according to claim 7, wherein said conjugated side-strapped phthalocyanine compound has a solubility in pyridine of at least 0.5±0.1 mole/L.

10. The composition according to claim 7, wherein said composition comprises a thin film of said conjugated side-strapped phthalocyanine compound.

11. The composition according to claim 10, wherein the hole mobility within said thin film is at least 0.10±0.02 $cm^2V^{-1}s^{-1}$.

12. The composition according to claim 10, wherein the hole mobility within said thin film is at least 0.90±0.18 $cm^2V^{-1}s^{-1}$.

13. The composition according to claim 10, wherein said thin film comprises ABAB stacking of said conjugated side-strapped phthalocyanine compound.

* * * * *